United States Patent
Brandle et al.

(10) Patent No.: US 7,361,331 B2
(45) Date of Patent: Apr. 22, 2008

(54) PLANT BIOREACTORS

(75) Inventors: Jim Brandle, London (CA); Shengwu Ma, London (CA); Rima Menassa, London (CA); Anthony Jevnikar, London (CA); Terry Delovitch, 1560 Gloucester Road, London, Ontario (CA) N6G 2S6

(73) Assignees: Her Majesty The Queen in Right of Canada, as represented by the Minister of Agriculture and Agri-Food, London, Ontario (CA); London Health Sciences Centre Research Inc., London, Ontario (CA); Terry Delovitch, Ontario (CA)

( * ) Notice: Subject to any disclaimer, the term of this patent is extended or adjusted under 35 U.S.C. 154(b) by 0 days.

(21) Appl. No.: 10/137,647

(22) Filed: May 3, 2002

(65) Prior Publication Data

US 2003/0135887 A1 Jul. 17, 2003

Related U.S. Application Data

(63) Continuation-in-part of application No. 09/773,385, filed on Feb. 1, 2001, now abandoned, which is a continuation of application No. 09/102,050, filed on Jun. 22, 1998, now abandoned, which is a continuation-in-part of application No. 08/733,791, filed on Oct. 18, 1996, now abandoned.

(51) Int. Cl.
*A61K 45/00* (2006.01)
*A01H 1/00* (2006.01)
*C07H 21/01* (2006.01)

(52) U.S. Cl. .......... 424/85.2; 424/278.1; 800/288; 800/294; 536/23.5

(58) Field of Classification Search ............ 424/85.2, 424/439; 435/414; 800/278, 288
See application file for complete search history.

(56) References Cited

U.S. PATENT DOCUMENTS

| | | | |
|---|---|---|---|
| 4,183,364 A | 1/1980 | Gumushan et al. | |
| 4,956,282 A | 9/1990 | Goodman et al. | |
| 5,260,205 A | 11/1993 | Nakatani et al. | |
| 5,316,931 A | 5/1994 | Donson et al. | |
| 5,368,854 A * | 11/1994 | Rennick ............ | 424/85.2 |
| 5,369,023 A | 11/1994 | Nakatani et al. | |
| 5,475,086 A | 12/1995 | Tobin et al. | |
| 5,487,991 A * | 1/1996 | Vandekerckhove et al. ............ | 435/69.1 |
| 5,550,038 A | 8/1996 | Goodman et al. | |
| 5,645,998 A | 7/1997 | Atkinson et al. | |
| 5,674,978 A | 10/1997 | Tobin et al. | |
| 5,705,626 A | 1/1998 | Tobin et al. | |
| 5,710,251 A | 1/1998 | Vellekamp et al. | |
| 5,762,937 A | 6/1998 | Atkinson et al. | |
| 5,837,812 A | 11/1998 | Harrison et al. | |
| 5,846,740 A | 12/1998 | Tobin et al. | |
| 5,929,304 A | 7/1999 | Radin et al. | |
| 5,998,366 A | 12/1999 | Tobin et al. | |
| 6,001,360 A | 12/1999 | Atkinson et al. | |
| 6,011,139 A | 1/2000 | Tobin et al. | |
| 6,211,352 B1 | 4/2001 | Harrison et al. | |
| 6,338,850 B1 | 1/2002 | Jevnikar et al. | |

FOREIGN PATENT DOCUMENTS

| | | |
|---|---|---|
| CA | 2188220 | 4/1998 |
| EP | 0 010 665 | 5/1980 |
| EP | 0 302 429 A1 | 2/1989 |
| EP | 0 437 320 A1 | 7/1991 |
| EP | 0 486 214 A2 | 5/1992 |
| GB | 2 218 420 A | 11/1989 |
| WO | WO 93/03161 | 2/1993 |
| WO | WO 95/08347 * | 3/1995 |
| WO | WO 95/15678 | 6/1995 |
| WO | WO 96/26218 | 8/1996 |
| WO | WO 97/04122 | 2/1997 |
| WO | WO 99/67401 | 12/1999 |
| WO | WO 00/20612 | 4/2000 |

OTHER PUBLICATIONS

Magnuson et al. (1998), Secretion of Biologically Active Human Interleukin-2 and Interleukin-4 from Genetically Modified Tobacco Cells in Suspension Culture, Prot. Exp. Purif. 13: 45-52.*

(Continued)

*Primary Examiner*—Robert Landsman
*Assistant Examiner*—Bruce D. Hissong
(74) *Attorney, Agent, or Firm*—Nixon & Vanderhye P.C.

(57) ABSTRACT

A plant expressing a cytokine and an autoantigen is disclosed. An example of a cytokine is a contra-inflammatory cytokine, for example IL-4 and IL-10, and an example of autoantigen is GAD. A novel method for the production of transgenic proteins of interest suitable for oral administration is also disclosed. Further, non-food crop plants expressing one or more proteins of interest are disclosed, as is a method involving the preparation of a protein of interest suitable for oral administration within a non-food crop plant comprising, transforming the non-food crop plant with a suitable vector containing a gene of interest and appropriate regulatory regions to ensure expression of the gene of interest within the non-food crop plant, such that the non-food crop plant is characterized as being non-toxic, non-addictive, palatable, and requiring minimal or no processing prior to oral administration. An example of a non-food crop plant is low alkaloid tobacco. Proteins of interest may include pharmaceutically active proteins such as growth regulators, insulin, interferons, interleukins, growth hormone, erythropoietin, G-CSF, GM-CSF, hPG-CSF, M-CSF, Factor VIII, Factor IX, tPA, antibodies, antigens and combinations and/or derivatives thereof.

18 Claims, 17 Drawing Sheets

OTHER PUBLICATIONS

Spurgeon (1999), Tobacco could be used to produce interleukin 10, BMJ 319(7203): 143.*

Duchmann et al. (1996), Tolerance towards resident intestinal flora in mice is abrogated in experimental colitis and restored by treatment with interleukin-10 or antibodies to interleukin-12, Eur. J. Immunol. 26(4): 934-938.*

Ma et al. (1997), Transgenic plants expressing autoantigens fed to mice to induce oral immune tolerance, Nat. Med. 3(7): 793-797.*

Brod et al. (1995), J. Interferon Cytokine Res. 15(2): 115-122.*

Hibi, et al. The Plant Cell 6: 723-735, 1994 'Gene expression in tobacco low-nicotine mutants'.*

Matsui, et al. J. Gastroenterol. 31: 6-11, 1996 'Control of gastric pH with ranitidine in patients with Crohn's disease receiving total parenteral nutrition. Comparison of two intravenous regimens'.*

Moore KW, et al. Interleukin-10. Annual Reivew of Immunology. 1993. vol. 11, p. 165-190.*

Spurgeon, D., *British Medical Journal*, vol. 319, No. 7203, Jul. 17, 1999, p. 143, "Tobacco could be used produce interleukin 10."

Sheibani, "Prokaryotic gene fusion expression systems and their use in structural and functional studies of proteins", Prep. Biochem. Biotechnol. 29(1):77-90 (1999)—Abstract.

Rais-Beghdadi et al, "Purification of recombinant proteins by chemical removal of the affinity tag", Appl. Biochem. Biotechnol. 74(2):95-103 (1998)—Abstract.

Zdanov et al, "Crystal structure of interleukin-10 reveals the functional dimer with an unexpected topological similarity to interferon γ", Structure 3(6):591-601 (1995).

Howard et al, "Interleukin 10 Protects Mice from Lethal Endotoxemia", J. Exp. Med. 177:1205-1208 (1993).

Gesser et al, "Identification of functional domains on human interleukin 10", Proc. Natl. Acad. Sci. USA 94:14620-14625 (1997).

Mason et al, "Expression of Norwalk virus capsid protein in transgenic tobacco and potato and its oral immunogenicity in mice", Proc. Natl. Acad. Sci. USA 93:5335-5340 (1996).

Chaplin, J.F., Proceedings of American Chemical Society Symposium, "Recent Advances in the Chemical Composition of Tobacco and Tobacco Smoke", th 173$^{rd}$ American Chem. Society Meeting Agric. & Food Chem. Division, New Orleans, Louisiana, pp. 330-337 (1997).

Arreaza et al, "Interleukin-4, Potential Immunoregulatory Agent in Therapy of Insulin-Dependent Diabetes Mellitus", Clin. Immunother. 6(4):1172-7039 (1996).

Schouten, et al, *Plant Molecular Biology*, 30: 781-793, 1996, "The C-terminal KDEL sequence increases the expression level of a single-chain antibody designed to be targeted to both the cytosol and the secretory pathway in transgenic tobacco."

Ma, J. K-C, et al, *Tibtech*, Dec. 1995, vol. 13, pp. 522-527, "Immunotherapeutic potential of antibodies produced in plants."

Haq, Tariq A., et al, *SCIENCE*, vol. 268, May 5, 1995, pp. 714-715, "Oral Immunization with a Recombinant Bacterial Antigen Produced in Transgenic Plants."

Ma, Julian K.-C., et al, *SCIENCE*, vol. 268, May 5, 1995, pp. 716-719, "Generation and Assembly of Secretory Antibodies in Plants."

Ma, S.-W., et al, *Nature Medicine*, vol. 3, No. 7, Jul. 1997, pp. 793-796, "Transgenic plants expressing autoantigens fed to mice to induce oral immune tolerance."

Burgess, Wilson H., et al, *The Journal of Cell Biology*, vol. 111, Nov. 1990, pp. 2129-2138, "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue."

Lazar, Elaine, et al, *Molecular And Cellular Biiology*, vol. 8, No. 3, Mar. 1988, p. 1247-1252, "Transforming Growth Factor α: Mutation of Aspartic Acid 47 and Leucine 48 Results in different Biological Activities."

Tao, Mi-Hua, et al, *Journal of Immunology*, vol. 143, No. 8, Oct. 15, 1989, pp. 2595-2601, "Studies of Aglycosylated Chimeric Mouse-Human IgG."

Gillies, Stephen D., et al, *Hum. Antibod. Hybridomas*, vol. 1, No. 1, pp. 47-54, "Antigen binding and Biological activities of engineered mutant chimeric antibodies with human tumor specificities."

Matsumoto, Shinya, et al, *Plant Molecular Biology*, 27: 1163-1172, 1995, "Characterization of a human glycoprotein (erythropoietin) produced in cultured tobacco cells."

Bosch, Dirk, et al, *Transgenic Research*, 3, 304-310 (1994), "A trout growth hormone is expressed, correctly folded and partially glycosylated in the leaves but not the seeds of transgenic plants."

Edelbaum, Orit, et al, *Journal of Interferon Research*, 12: 449-453 (1992), "Expression of Active Human Interferon-β in Transgenic Plants."

Kwon, Seok Yun, et al, *Mol. Cells*, vol. 5, No. 5, pp. 486-492, "Expression of Active Human Interleukin-6 in Transgenic Tobacco."

Frisch, David A., *Plant Molecular Biology* 27: 405-409 (1995), "Complete sequence of the binary vector Bin 19."

Vieira, P., et al, *Proc. Natl. Acd. Sci. USA*, vol. 88, pp. 1172-1176, Feb. 1991, "Isolation and expression of human cytoline synthesis inhibitory factor cDNA clones: Homology to Epstein-Barr virus open reading frame BCRFI."

Tisch et al, "Antigen-Specific Mediated Suppression of β Cell Autoimmunity by Plasmid DNA Vaccination", The Journal of Immunology 166(3):2122-2132 (2001).

Ma and Jevnikar, "Autoantigens Produced in Plants for Oral Tolerance Therapy of Autoimmune Diseases", Advances in Experimental Medicine and Biology 464:179-194 (1999).

Porceddu et al, "Transgenic plants expressing human glutamic acid decarboxylase (GAD65), a major autoantigen in insulin-dependent diabetes mellitus", Molecular Breeding 5:553-560 (1999).

Inobe et al, "IL-4 is a differentiation factor for transforming growth factor-β secreting Th3 cells and oral administration of IL-4 enhances oral tolerance in experimental allergic encephalomyelitis", Eur. J. Immunol. 28:2780-2790 (1998).

Menassa et al, "A self-contained system for the field production of plant recombination interleukin-10", Molecular Breeding 8:177-185 (2001).

Sato et al, "Regulatory Role of Endogenous Interleukin-10 in Cutaneous Inflammatory Response of Murine Wound Healing", Biochemical and Biophysical Research Communications 265:194-199 (1999).

Nelson et al, "Interleukin 10 Treatment Reduces Fibrosis in Patients With Chronic Hepatitis C: A Pilot Trial of Interferon Nonresponders", Gastroenterology 118:655-660 (2000).

Gadani et al, "Tobacco: a tool for plant genetic engineering research and molecular farming", Agro Food Industry Hi-Tech, Teknoszinze, Milan, IT 6:3-6 (1995).

van Rooijen and Moloney, "Structural Requirements of Oleosin Domains for Subcellular Targeting to the Oil Body", Plant Physiol. 109:1353-1361 (1995).

Jobling and Gehrke, "Enhanced translation of chimaeric messenger RNAs containing a plant viral untranslated leader sequence", Nature 325:622-625 (1987).

Syto et al, "Structural and Biological Stability of the Human Interleukin 10 Homodimer", Biochemistry 37:16943-16951 (1998).

Grimley et al, "Inhibition of intragastric acidity in healthy subjects dosed with ranitidine 75 mg: a comparative study with cimetidine and placebo", Aliment Pharmacol. Ther. 11:875-879 (1997).

Kühn et al, "Interleukin-10-Deficient Mice Develop Chronic Enterocolitis", Cell 75:263-274 (1993).

Bradford, "A Rapid and Sensitive Method for the Quantitation of Microgram Quantities of Protein Utilizing the Principle of Protein-Dye Binding", Analytical Biochemistry 72:248-254 (1976).

Miki et al, "XXV Transgenic Tobacco: Gene Expression and Applications", Biotechnology in Agriculture and Forestry 45:336-354 (1999).

Zheng et al, "Administration of Noncytolytic IL-10/Fc in Murine Models of Lipopolysaccharide-Induced Septic Shock and Allogenic Islet Transplantation", The Journal of Immunology 154:5590-5600 (1995).

Fiorentino et al, "IL-10 Inhibits Cytokine Production By Activated Macrophages", The Journal of Immunology 147:3815-3822 (1991).

Gegenheimer, "Preparation of Extracts from Plants", Methods in Enzymology 182:174-185 (1990).

Burnette, ""Western Blotting": Electrophoretic Transfer of Proteins from Sodium Dodecyl Sulfate-Polyacrylamide Gels to Unmodified Nitrocellulose and Radiographic Detection with Antibody and Radioiodinated Protein A", Analytical Biochemistry 112:195-203 (1981).

von Heijne, "A new method for predicting signal sequence cleavage sites", Nucleic Acids Research 14(11):4683-4690(1986).

Kay et al, "Duplication of CaMV 35S Promoter Sequences Creates a Strong Enhancer for Plant Genes", Science 236:1299-1302 (1987).

Sijmons et al, "Production of Correctly Processed Human Serum Albumin in Transgenic Plants", Bio/Technology 8:217-221 (1990).

Cornelissen et al, "Molecular characterization of messenger RNAs for 'pathogenesis-related' proteins 1a, 1b and 1c, induced by TMV infection of tobacco", The EMBO Journal 5(1):37-40 (1986).

Sleat et al, "Studies of the mechanism of translational enhancement by the 5'-leader sequence of tobacco mosaic virus RNA", Eur. J. Biochem. 175:75-86 (1988).

Richards et al, "Leader sequence of 71 nucleotides devoid of G in tobacco mosaic virus RNA", Nature 267:548-550 (1977).

Richards et al, "Nucleotide Sequence at the 5' Extremity of Tobacco-Mosaic-Virus RNA", Eur. J. Biochem. 84:513-519 (1978).

Hiatt et al, "Production of antibodies in transgenic plants", Nature 342:76-78 (1989).

Denecke et al, "Protein Secretion in Plant Cells Can Occur via a Default Pathway", The Plant Cell 2:51-59 (1990).

Slavin et al, "Mucosal administration of IL-10 enhances oral tolerance in autoimmune encephalomyelitis and diabetes", International Immunology 13(6):825-833 (2001).

Fiocchi, "Cytokines and Animal Models: A Combined Path to Inflammatory Bowel Disease Pathogenesis", Gastroenterology 104:1202-1205 (1993).

Rollwagen and Baqar, "Oral cytokine administration", Immunology Today 17(12):548550 (1996).

Steidler et al, "Treatment of Murine Colitis by *Lactococcus lactis* Secreting Interleukin-10", Science 289:1352-1355.

Schreiber et al, "Safety and Efficacy of Recombinant Human Interleukin 10 in Chronic Active Crohn's Disease", Gastroenterology 119:1461-1472 (2000).

Fedorak et al, "Recombinant Human Interleukin 10 in the Treatment of Patients With Mild to Moderately Active Crohn's Disease", Gastroenterology 119:1473-1482 (2000).

Leach et al, "The Role of IL-10 in Inflammatory Bowel Disease" "Of Mice and Men", Toxicologic Pathology 27(1):123-133 (1999).

Arakawa et al, "A plant-based cholera toxin B subunit-insulin fusion protein protects against the development of autoimmune diabetes", Nature Biotechnology 16:934-938 (1998).

Montanari et al, "Tobacco Fraction 1 Protein (F1P) Utilization for Oral or Enteral Feedings of Patients. 1. Heavy Metal Evaluation", LWT 26(3):259-263 (1993).

Woodlief et al, "Effect of Variety and Harvest Treatments on Protein Yield of Close-Grown Tobacco", Tobacco Science XXV:83-86 (1981).

Kong et al, "Oral immunization with hepatitis B surface antigen expressed in transgenic plants", Proc. Natl. Acad. Sci. USA 98(20):11539-11544 (2001).

Fiorentino et al. "Two types of mouse T helper cell—IV. Th2 clones secrete a factor that inhibits cytokine prodution by Th1 clones" J. Exp. Med. 170:2081-2095 (1989).

* cited by examiner

A.

```
                                        #4361
                 ACAATTACCAACAACAACAACAACAACAACATTACAATTACTATTTA
                 #1309
                 ACAATTACCAACAACAACAACAACAACAACATTACAATTACTATTTACAATTACAA
    BamHI  XhoI
5' |GATCCTC|GAGTATTTTACA
3'         |GAGCTCATAAAATGTTGTTAATGGTTGTTGTTGTTGTTGTTGTTGTAATGTTAATGATAAATGTTAATGT|
    #1091
    #1092
```

B.

```
                                                                #4363
                                                TCAGTACTCTTCTCTTATTCCTGATCATATC
    #4362
5' |CAATTACAA|ATG|GGATTTTTTCTCTTTTCACAAATGCCAAGCTTTTTCTTG
3'           ACCCTAAAAAAGAGAAAAGTGTTTACGGTTCGAAAAAGAACAGTCATGAGAGAG
              #4364                                              AATAAGGACTAGTATAG
                                                                 #4365

5' TCACTCTTCGCATGC
3' AGTGAGAAGCGTACGAT
```

C.

MetGlyPhePheLeuPheSerGlnMetProSerPhePheLeuValSerThrLeuLeuLeuPheLeuIleIle
    SerHisSerSerHisAla

FIGURE 10 hIL10-5'-BamHI

<u>GGATCC</u>ACAAGACAGACTTGCAAAAGAAGG　　　　Signal peptide
1　aaaccacaagacagacttgcaaaagaaggcatgcacagctcagcactgctctgttgcctg
　　　　　　　　　　　　　　　　　　　M　H　S　A　L　L　C　C　L 61　gtcctcctgactggggtgagggccagcccaggccagggcacccagtctgagaacagctgc
　　V　L　L　T　G　V　R　A　S　P　G　Q　G　T　Q　S　E　N　S　C 121　acccacttcccaggcaacctgcctaacatgcttcgagatctccgagatgccttcagcaga
　　　T　H　F　P　G　N　L　P　N　M　L　R　D　L　R　D　A　F　S　R 181　gtgaagactttctttcaaatgaaggatcagctggacaacttgttgttaaaggagtccttg
　　　V　K　T　F　F　Q　M　K　D　Q　L　D　N　L　L　L　K　E　S　L 241　ctggaggactttaaggggttacctgggttgccaagccttgtctgagatgatccagttttac
　　　L　E　D　F　K　G　Y　L　G　C　Q　A　L　S　E　M　I　Q　F　Y 301　ctggaggaggtgatgccccaagctgagaaccaagacccagacatcaaggcgcatgtgaac
　　　L　E　E　V　M　P　Q　A　E　N　Q　D　P　D　I　K　A　H　V　N 361　tccctgggggagaacctgaagaccctcaggctgaggctacggcgctgtcatcgatttctt
　　　S　L　G　E　N　L　K　T　L　R　L　R　L　R　R　C　H　R　F　L 421　ccctgtgaaaacaagagcaaggccgtggagcaggtgaagaatgcctttaataagctccaa
　　　P　C　E　N　K　S　K　A　V　E　Q　V　K　N　A　F　N　K　L　Q 481　gagaaaggcatctacaaagccatgagtgagtttgacatcttcatcaactacatagaagcc
　　　E　K　G　I　Y　K　A　M　S　E　F　D　I　F　I　N　Y　I　E　A hIL-10-His-KDEL
　　　　M　T　M　K　I　R　N　L　V　P　R　G　S　S　S　G　H　H　H
　　　<u>TACTGTTACTTCTATGCATTGGAACAGGGTGCGCCAAGAAGAAGACCAGTAGTAGTA</u>
541　tacatgacaatgaagatacgaaactgagacatcagggtggcgactctatagactctagga
　　　Y　M　T　M　K　I　R　N　*

H　H　H　K　D　E　L　*
　　　<u>GTAGTAGTGTTCCTGCTCGAGA</u>CTTAAGGG
601　cataaattagaggtctccaaaatcggatct　ggggctctgg　gatagctgac　ccagccctt 661　gagaaacctt　attgtacctc　tcttatagaa　tatttattac　ctctgatacc　tcaaccccca
　　　　　　　　　　　　　　　　　　　　　　　　　　　　　　GG AGTTGGGGGT
　　　　　　　　　　　　　　　　　　　　　　　　　　　　　　←

721　tttctattta　tttactgagc　ttctctgtga　acgatttaga　aagaagccca　atattataat
　　　AAAGATAAAT　AACTTAAGG
　　　　hIL10-3'-EcoRI 781　ttttttcaat　atttattatt　ttcacctgtt　tttaagctgt　ttccataggg　tgacacacta
841　tggtatttga　gtgttttaag　ataaattata　agttacataa　gggaggaaaa　aaaatgttct
901　ttggggagcc　aacagaagct　tccattccaa　gcctgaccac　gctttctagc　tgttgagctg
961　ttttccctga　cctccctcta　atttatcttg　tctctgggct　tggggcttcc　taactgctac
1021　aaatactctt　aggaagagaa　accagggagc　ccctttgatg　attaattcac　cttccagtgt
1081　ctcggaggga　ttcccctaac　ctcattcccc　aaccacttca　ttcttgaaag　ctgtggccag
1141　cttgttattt　ataacaacct　aaatttggtt　ctaggcgggg　cgcggtggct　cacgcctgta
1201　atcccagcac　tttgggaggc　tgaggcgggt　ggatcacttg　aggtcaggag　ttcctaacca
1261　gcctggtcaa　catggtgaaa　ccccgtctct　actaaaaata　caaaaattag　ccgggcatgg
1321　tggcgcgcac　ctgtaatccc　agctacttgg　gaggctgagg　caagagaatt　gcttgaaccc
1381　aggagatgga　agttgcagtg　agctgatatc　atgccctgt　actccagcct　gggtgacaga
1441　gcaagactct　gtctcaaaaa　aataaaaata　aaaataaatt　tggttctaat　agaactcagt
1501　tttaactaga　atttattcaa　ttcctctggg　aatgttacat　tgtttgtctg　tcttcatagc
1561　agatttaat　tttgaataaa　taaatgtatc　ttattcacat　c

FIGURE 14

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Description of Artificial Sequence:primer

<400> SEQUENCE: 1
gatcctcgag tatttttaca                                              20

<210> SEQ ID NO 2
<211> LENGTH: 58
<212> TYPE: DNA
<213> ORGANISM: Artificial sequence
<220> FEATURE:
<223> OTHER INFORMATION: Description of Artificial Sequence:primer

<400> SEQUENCE: 2
acaattacca acaacaacaa acaacaaaca acattacaat tactatttac aattacaa    58

<210> SEQ ID NO 3
<211> LENGTH: 49
<212> TYPE: DNA
<213> ORGANISM: Artificial sequence
<220> FEATURE:
<223> OTHER INFORMATION: Description of Artificial Sequence:primer

<400> SEQUENCE: 3
acaattacca acaacaacaa acaacaaaca acattacaat tactattta              49

<210> SEQ ID NO 4
<211> LENGTH: 74
```

```
<212> TYPE: DNA
<213> ORGANISM: Artificial sequence
<220> FEATURE:
<223> OTHER INFORMATION: Description of Artificial Sequence:primer

<400> SEQUENCE: 4
ttgtaattgt aaatagtaat tgtaatgttg tttgttgttt gttgttgttg gtaattgttg      60
taaaaatact cgag                                                       74

<210> SEQ ID NO 5
<211> LENGTH: 51
<212> TYPE: DNA
<213> ORGANISM: Artificial sequence
<220> FEATURE:
<223> OTHER INFORMATION: Description of Artificial Sequence:primer

<400> SEQUENCE: 5
caattacaat gggattttt ctcttttcac aaatgccaag cttttttctt g                51

<210> SEQ ID NO 6
<211> LENGTH: 46
<212> TYPE: DNA
<213> ORGANISM: Artificial sequence
<220> FEATURE:
<223> OTHER INFORMATION: Description of Artificial Sequence:primer

<400> SEQUENCE: 6
tcagtactct tctcttattc ctgatcatat ctcactcttc gcatgc                    46

<210> SEQ ID NO 7
<211> LENGTH: 30
<212> TYPE: PRT
<213> ORGANISM: Artificial sequence
<220> FEATURE:
<223> OTHER INFORMATION: Description of Artificial Sequence:primer

<400> SEQUENCE: 7

Met Gly Phe Phe Leu Phe Ser Gln Met Pro Ser Phe Phe Leu Val Ser
1               5                  10                  15
Thr Leu Leu Leu Phe Leu Ile Ile Ser His Ser Ser His Ala
            20                  25                  30

<210> SEQ ID NO 8
<211> LENGTH: 56
<212> TYPE: DNA
<213> ORGANISM: Artificial sequence
<220> FEATURE:
<223> OTHER INFORMATION: Description of Artificial Sequence:primer

<400> SEQUENCE: 8
gagaagagta ctgacaagaa aaaagcttgg catttgtgaa aagagaaaaa atccca          56

<210> SEQ ID NO 9
<211> LENGTH: 34
<212> TYPE: DNA
<213> ORGANISM: Artificial sequence
<220> FEATURE:
<223> OTHER INFORMATION: Description of Artificial Sequence:primer

<400> SEQUENCE: 9
tagcatgcga agagtgagat atgatcagga ataa                                 34

<210> SEQ ID NO 10
<211> LENGTH: 26
<212> TYPE: DNA
```

<213> ORGANISM: Artificial sequence
<220> FEATURE:
<223> OTHER INFORMATION: Description of Artificial Sequence:primer

<400> SEQUENCE: 10
tattttttac aacaattacc aacaac        26

<210> SEQ ID NO 11
<211> LENGTH: 23
<212> TYPE: DNA
<213> ORGANISM: Artificial sequence
<220> FEATURE:
<223> OTHER INFORMATION: Description of Artificial Sequence:primer

<400> SEQUENCE: 11
cagcagtcat ctgcatacag cac        23

<210> SEQ ID NO 12
<211> LENGTH: 1645
<212> TYPE: DNA
<213> ORGANISM: Artificial sequence
<220> FEATURE:
<223> OTHER INFORMATION: Description of Artificial Sequence:primer

<400> SEQUENCE: 12

| | | |
|---|---|---|
| aaaccacaag acagacttgc aaaagaaggc atgcacagct cagcactgct ctgttgcctg | 60 |
| gtcctcctga ctggggtgag ggccagccca ggccagggca cccagtctga aacagctgc | 120 |
| acccacttcc caggcaacct gcctaacatg cttcgagatc tccgagatgc cttcagcaga | 180 |
| gtgaagactt tctttcaaat gaaggatcag ctggacaact tgttgttaaa ggagtccttg | 240 |
| ctggaggact ttaagggtta cctgggttgc aagccttgt ctgagatgat ccagttttac | 300 |
| ctggaggagg tgatgcccca agctgagaac caagacccag acatcaaggc gcatgtgaac | 360 |
| tccctggggg agaacctgaa gaccctcagg ctgaggctac ggcgctgtca tcgatttctt | 420 |
| ccctgtgaaa acaagagcaa ggccgtggag caggtgaaga atgcctttaa taagctccaa | 480 |
| gagaaaggca tctacaaagc catgagtgag tttgacatct tcatcaacta catagaagcc | 540 |
| tacatgacaa tgaagatacg aaactgagac atcagggtgg cgactctata gactctagga | 600 |
| cataaattag aggtctccaa aatcggatct ggggctctgg gatagctgac ccagccctt | 660 |
| gagaaacctt attgtacctc tcttatagaa tatttattac ctctgatacc tcaacccca | 720 |
| tttctattta tttactgagc ttctctgtga acgatttaga agaagcccca atattataat | 780 |
| ttttttcaat atttattatt ttcacctgtt tttaagctgt ttccataggg tgacacacta | 840 |
| tggtatttga gtgttttaag ataaattata agttacataa gggaggaaaa aaaatgttct | 900 |
| ttggggagcc aacagaagct tccattccaa gcctgaccac gctttctagc tgttgagctg | 960 |
| ttttccctga cctccctcta atttatcttg tctctgggct tggggcttcc taactgctac | 1020 |
| aaatactctt aggaagagaa accagggagc cccttttgatg attaattcac cttccagtgt | 1080 |
| ctcggaggga ttcccctaac ctcattcccc aaccacttca ttcttgaaag ctgtggccag | 1140 |
| cttgttattt ataacaacct aaatttggtt ctaggccggg cgcggtggct cacgcctgta | 1200 |
| atcccagcac tttgggaggc tgaggcgggt ggatcacttg aggtcaggag ttcctaacca | 1260 |
| gcctggtcaa catggtgaaa ccccgtctct actaaaaata caaaaattag ccgggcatgg | 1320 |
| tggcgcgcac ctgtaatccc agctacttgg gaggctgagg caagagaatt gcttgaaccc | 1380 |
| aggagatgga agttgcagtg agctgatatc atgcccctgt actccagcct gggtgacaga | 1440 |
| gcaagactct gtctcaaaaa aataaaaata aaaataaatt tggttctaat agaactcagt | 1500 |

```
tttaactaga atttattcaa ttcctctggg aatgttacat tgtttgtctg tcttcatagc    1560 agatttttaat tttgaataaa taaatgtatc ttattcacat caaaaaaaaa aaaaaaaaaa    1620
ctcgaggggg ggccggtacc caatg                                           1645
```

<210> SEQ ID NO 13
<211> LENGTH: 27
<212> TYPE: DNA
<213> ORGANISM: Artificial sequence
<220> FEATURE:
<223> OTHER INFORMATION: Description of Artificial Sequence:primer

<400> SEQUENCE: 13

```
aatctcgagc atatccacgg atgcgac                                          27
```

<210> SEQ ID NO 14
<211> LENGTH: 29
<212> TYPE: DNA
<213> ORGANISM: Artificial sequence
<220> FEATURE:
<223> OTHER INFORMATION: Description of Artificial Sequence:primer

<400> SEQUENCE: 14

```
ataggtaccg taatccattt gcatgatgc                                        29
```

<210> SEQ ID NO 15
<211> LENGTH: 27
<212> TYPE: DNA
<213> ORGANISM: Artificial sequence
<220> FEATURE:
<223> OTHER INFORMATION: Description of Artificial Sequence:primer

<400> SEQUENCE: 15

```
aattccatgg catctccggg ctctggc                                          27
```

<210> SEQ ID NO 16
<211> LENGTH: 34
<212> TYPE: DNA
<213> ORGANISM: Artificial sequence
<220> FEATURE:
<223> OTHER INFORMATION: Description of Artificial Sequence:primer

<400> SEQUENCE: 16

```
ataatctaga tttaaatct tgtccaaggc gttc                                   34
```

<210> SEQ ID NO 17
<211> LENGTH: 36
<212> TYPE: DNA
<213> ORGANISM: Artificial sequence
<220> FEATURE:
<223> OTHER INFORMATION: Description of Artificial Sequence:primer

<400> SEQUENCE: 17

```
ttaatctaga ccatggcgtc ttcgacccca tcttcg                                36
```

<210> SEQ ID NO 18
<211> LENGTH: 34
<212> TYPE: DNA
<213> ORGANISM: Artificial sequence
<220> FEATURE:
<223> OTHER INFORMATION: Description of Artificial Sequence:primer

<400> SEQUENCE: 18

```
ttaatctaga ttacagatcc tggcccagtc tttc                                  34
```

<210> SEQ ID NO 19
<211> LENGTH: 24
<212> TYPE: DNA
<213> ORGANISM: Artificial sequence
<220> FEATURE:
<223> OTHER INFORMATION: Description of Artificial Sequence:primer

<400> SEQUENCE: 19
aatccatggc atctccgggc tctg                                              24

<210> SEQ ID NO 20
<211> LENGTH: 27
<212> TYPE: DNA
<213> ORGANISM: Artificial sequence
<220> FEATURE:
<223> OTHER INFORMATION: Description of Artificial Sequence:primer

<400> SEQUENCE: 20
atatctagat aaatcttgtc caaggcg                                           27

<210> SEQ ID NO 21
<211> LENGTH: 477
<212> TYPE: DNA
<213> ORGANISM: Artificial sequence
<220> FEATURE:
<223> OTHER INFORMATION: Description of Artificial Sequence:primer

<400> SEQUENCE: 21
atggcacttc caattagcaa agttgatttc ttaatattta tgtgtcttat aggattaggg       60
tcagctctcg agctaatcca cggatgcgac aaaaatcact tgagagagat catcggcatt      120
ttgaacgagg tcacaggaga agggacgcca tgcacggaga tggatgtgcc aaacgtcctc      180
acagcaacga agaacaccac agagagtgag ctcgtctgta gggcttccaa ggtgcttcgt      240
atattttatt taaaacatgg gaaaactcca tgcttgaaga agaactctag tgttctcatg      300
gagctgcaga gactctttcg ggcttttcga tgcctggatt catcgataag ctgcaccatg      360
aatgagtcca gtccacatc actgaaagac ttcctggaaa gcctaaagag catcatgcaa      420
atggattact cgggtaccca tcatcatcat catcattctg agaaagatga gctatga         477

<210> SEQ ID NO 22
<211> LENGTH: 459
<212> TYPE: DNA
<213> ORGANISM: Artificial sequence
<220> FEATURE:
<223> OTHER INFORMATION: Description of Artificial Sequence:primer

<400> SEQUENCE: 22
atggcacttc caattagcaa agttgatttc ttaatattta tgtgtcttat aggattaggg       60
tcagctctcg agctaatcca cggatgcgac aaaaatcact tgagagagat catcggcatt      120
ttgaacgagg tcacaggaga agggacgcca tgcacggaga tggatgtgcc aaacgtcctc      180
acagcaacga agaacaccac agagagtgag ctcgtctgta gggcttccaa ggtgcttcgt      240
atattttatt taaaacatgg gaaaactcca tgcttgaaga agaactctag tgttctcatg      300
gagctgcaga gactctttcg ggcttttcga tgcctggatt catcgataag ctgcaccatg      360
aatgagtcca gtccacatc actgaaagac ttcctggaaa gcctaaagag catcatgcaa      420
atggattact cgggtaccctc tgagaaagat gagctatga                            459

PLANT BIOREACTORS

This application is a Continuation-In-Part of Ser. No. 09/773,385, filed Feb. 1, 2001 now abandoned, which is a Continuation application of Ser. No. 09/102,050, filed Jun. 22, 1998 now abandoned, which is a Continuation-In-Part application of Ser. No. 08/733,791, filed Oct. 18, 1996 now abandoned.

The present invention relates to the use of plants as a bioreactor for the production of heterologous proteins. More specifically this invention relates to the expression of transgenes of interest for oral administration using plants.

BACKGROUND OF THE INVENTION

Expression of mammalian genes in several plants including tobacco and *Arabidopsis* has been recognized as efficient, low cost, non-sterile bioreactors for the production of proteins valuable to both medicine and industry (Ma and Hein 1995). Recently, evidence was presented that demonstrated that the four chains of the secretory immunoglobulin were properly expressed and assembled in plants and that the antibody was fully functional (Ma et al 1995). Furthermore, bacterial (Haq et al 1995), and viral (Mason et al 1996) antigens produced in transgenic tobacco and potato effectively immunized mice when the transgenic potato was administered orally. Oral administration of protein antigens can result in a diminished immune response to subsequent systemic administration (eg., by injection) of the same antigen, a process known as oral tolerance (Mowat, 1987). Oral tolerance has recently been explored as a potential antigen-specific immunotherapeutic strategy for the treatment of organ-specific autoimmune diseases. In animal models, oral administration of disease inducing autoantigens has been shown to inhibit several experimental autoimmune diseases, including animal NOD diabetes, uveoretinitis, experimental autoimmune encephalomyelitis (EAE), and rheumatoid arthritis (RA). However, one limitation with clinical use of the oral tolerance approach is the cost of protein production, as oral tolerance requires the ingestion of relatively large amounts of protein antigens, often in excess of quantities that can be provided by conventional protein synthesis or fermentation systems.

As the immune system is specific in the recognition of protein antigens, it is preferred that the antigens are mammalian and species specific to elicit the desired reduction in antigen directed immune responses. The use of plants as an expression system for the production of mammalian antigen proteins offers unique advantages beyond high production yields at competitive low cost. These advantages include reduced health risks from possible pathogen contamination as would be the case with extraction from mammalian tissues, correct modification and assembly of protein leading to function of proteins expressed by the plant when required or desired, optimization of high expression levels, and the ability to induce oral immune tolerance without extensive purification of the plant material. Using edible plant tissue leads to major cost reductions due to the simplicity of the delivery system.

Peripheral immune responses can be downregulated with oral administration of protein antigens, and this effect is antigen and protein specific. Human volunteers fed keyhole limpet hemocyanin (KLH) demonstrated reduced peripheral immune responses to KLH on recall responses of lymphocytes re-exposed to that antigen in vitro (Matsui, M. et al., 1996, Ann NY Acad Sci 778:398-404). Therefore, oral tolerance can be demonstrated in humans. The magnitude of response may be influenced by several factors, including expression levels of the transgenic protein of interest within plants, or the presence of immune adjuvants or response modifiers present within the composition.

Plants also may represent an ideal expression system for oral immune tolerance for several additional factors. Firstly, immune tolerance requires activation events within T lymphocytes, and plants by their composition which includes lectins may facilitate this. Additionally, the accumulation of transgenic proteins within plant cell compartments may protect the antigen from degradation in the digestive tract. This could augment oral immune tolerance by delivering transgenic plant protein to effector sites in the gut distal to the digestive environment of the stomach and duodenum (e.g. Kong et al, 2001, P.N.A.S, 98:11539-11544).

The use of plants as an expression system for production of mammalian antigenic proteins offers several unique advantages, including high production yields at competitive low cost, reduced health risks from pathogen contamination, and correct modification and assembly of foreign proteins. An additional advantage of a plant production system is that proteins, in the case of oral immune tolerance induction, may be used directly without extensive purification resulting in further cost reductions. In this regard it has been noted that proteins produced in transgenic tobacco required purification prior to administration. Clearly steps involving purification or processing are undesirable if ease of oral administration is to be maximized as well as minimizing any associated costs for production.

Numerous plants have proven themselves to be amenable to transformation with heterologous genes and for some time tobacco has been the model system for plant transformation. Despite the fact that crop-protection focused biotechnologies have not found application in non-food crop plant production, a major role does remain for such plants as bioreactors. An example of a non-food crop plant is tobacco, which is capable of producing high levels of soluble protein (fraction 1 protein, F1P; Woodleif et al 1981) and pilot systems have been developed to purify this fraction for use as a high protein dietary supplement (Montanari et al 1993).

From both a regulatory and public safety stand point non-food crop plants are ideal species for the transgenic production of biologically active proteins. Non-food crop plants minimize the risk of accidental leakage of transgenic plant material expressing genes for biologically active proteins into the human food chain. Other plant bioreactor systems based on canola (Rooijen et al. 1995), potato (Manson et al 1996), rice and cassava (Ma and Hein 1995) do not offer this advantage. Furthermore, non-food crop plants can be selected so that production in areas where there are no naturally occurring wild species further minimizes the risk of gene leakage to the local flora, an example of this would be to grow tobacco in regions where tobacco does not overwinter, such as Canada. With any non-food crop plant, transgenic proteins can be produced using any tissue or organ of the plant. However if protein production is based on leaves, not seeds or tubers, and when coupled with the fact that the leaves are harvested before flowering there is virtually no risk of uncontrolled bioreactor plants occurring in future crop seasons.

However, many non-food crop plants contain high levels of secondary plant products making plant tissue obtained from these plants unsuitable for direct oral administration. Earlier studies have described the administration of tobacco-derived proteins to mice, however, the proteins were in a partially purified form. For example the study by Mason et al (1996) involved the direct oral administration of viral antigens expressed in potato tuber and tobacco. The potato tuber samples were directly fed to mice, yet the antigen, when obtained from tobacco, had to be partially purified using sucrose gradients prior to administration to mice.

The breeding of low alkaloid-containing tobacco plants has been reported (Chaplin 1977), however, use of such a plant as a bioreactor has not been suggested. Recently, specific alteration of nicotine levels within tobacco, by either over expression (i.e. increasing) or antisense expression (decreasing) of putrescine N-methyltransferase, a rate limiting enzyme involved in the nicotine biosynthetic pathway, has been suggested (U.S. Pat. No. 5,260,205, issued Nov. 9, 1993 and U.S. Pat. No. 5,369,023, issued Nov. 29, 1994; inventors Nakatani and Malik). However, these methods are directed to the alteration of nicotine levels so that the levels of other alkaloids that affect the flavours and aroma of tobacco are not modified in any manner. These plants are not ideal for use as a non-food crop plant as describe herein, since the levels of only a select group of alkaloids have been reduced. Further, no nicotine free plants were actually produced, nor was the use of these transgenically modified tobacco plants, as a bioreactor for the synthesis of proteins of interest, suggested. However, such methods may be used and augmented in order to produce non-food crop plants where the total alkaloid level is reduced. Such an approach may be useful for the production of low alkaloid plants as a bioreactor for the synthesis of proteins of interest as contemplated by this invention.

U.S. Pat. No. 6,338,850 and EP 720, 484 discloses the expression of glutamic acid decarboxylase within a plant.

Oral tolerance has been explored as a potential antigen specific immunotherapeutic strategy for the treatment of organ specific autoimmune disease and prevention of transplantation and rejection. However, there are several potential limitations in the success of this approach in human disease, including selection of the appropriate antigen that is specific to disease, intervention in the disease process prior to onset of marked epitope spreading in which the targeting of the initial peptide is extended to associated peptides within the triggering protein, intervention in the disease process prior to onset of advanced clinical symptoms, and the requirement for large amounts of protein antigen suitable for clinical use. This latter issue leads to large costs of protein production from the use of conventional expression systems including transgenic expression in tissue culture and fermentation systems, to produce the amounts of protein needed. Additionally, expression in bacterial systems incapable of glycosylation and correct folding of the protein, leads to the formation of inclusion bodies and marked reduction in levels of recoverable usable protein antigens.

There is a need in the art for a method of making proteins in large quantities and at low cost. Further there is a need in the art for making biologically active proteins in large quantities and low cost, that do not require purification or further processing prior to being administered to a subject. Furthermore, there is a need for enhancing the action of an autoantigen, for example by co-administration of the autoantigen with a cytokin.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the use of plants as a bioreactor for the production of heterologous proteins. More specifically this invention relates to the expression of transgenes of interest for oral administration using plants.

The present invention provides a plant, or portion thereof, comprising one or more nucleotide sequences conferring the ability of the plant, or portion thereof, to express a cytokine. The cytokine may be selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-26, IL-27, EPO, CSF, G-CSF, GM-CSF, hPG-CSF, M-CSF, Factor VIII, Factor IX, tPA, hGH, growth factor, epidermal growth factor, keratinocyte growth factor, and transformation growth factor. Furthermore, the cytokine may be a member of the IL-10 family, a contra inflammatory cytokine.

The present invention also provides a plant, or portion thereof, as described above further comprising a nucleotide sequence conferring the ability of said plant, or portion thereof to express glutamic acid decarboxylase (GAD), or a fragment of GAD.

According to the present invention, there is provided a plant, or portion thereof, comprising one or more nucleotide sequences conferring the ability of said plant, or portion thereof to express IL-4 and GAD. In an embodiment which is not meant to be limiting, the plant is a tobacco plant. In a further aspect of an embodiment, the tobacco plant is a low-nicotine, low-alkaloid tobacco plant, such as but not limited to 81V-9.

Also provided by the present invention as defined above, the IL-4 and GAD may comprise sequences from different species, or the IL-4 and GAD may comprise sequences from the same species. The IL-4 and GAD may be selected from, but are not limited to being selected from the group consisting of:
  a) murine IL-4 and murine GAD 67;
  b) murine IL-4 and murine GAD 65;
  c) murine IL-4 and human GAD 67;
  d) murine IL-4 and human GAD 65;
  e) human IL-4 and human GAD 67;
  f) human IL-4 and human GAD 65;
  g) human IL-4 and murine GAD 67;
  h) human IL-4 and murine GAD 67;
  i) human IL-4, murine IL-4, or a combination thereof and,
  j) murine GAD 67, murine GAD 65, human GAD 65, human GAD 67, or a combination thereof.

According to the present invention, there is provided a composition comprising an plant-expressed cytokine, and an autoantigen. In an embodiment the cytokine is a contra-inflammatory cytokine and the autoantigen is GAD or a fragment thereof. The cytokine and autoantigen may be produced in the same plant or in different plants. For example, but not wishing to be limiting, the cytokine may be produced in a first plant, and the autoantigen may produced in a second plant.

The present invention pertains to a method of treating an auto-immune disease in a subject comprising, orally administering to the subject a composition comprising a plant-expressed contra-inflammatory cytokine, and an autoantigen, a contra-inflammatory cytokine, and a plant-expressed autoantigen, or a plant-expressed contra-inflammatory cytokine, and a plant-expressed autoantigen.

Also provided in the present invention is a method of producing a cytokine for oral administration comprising, transforming a plant, or portion thereof with a nucleotide sequence encoding the cytokine, growing the plant, and expressing the cytokine in the plant, or a portion thereof.

Further, the present invention provides a method of eliciting an immune response against an antigen in a subject, the method comprising orally administering a plant or portion thereof comprising an antigen and an cytokine to the subject. The antigen may be an autoantigen, for example, but not limited to GAD. Further, the cytokine may comprise a contra-inflammatory cytokine. Preferably the autoantigen and cytokine comprise sequences which are naturally present in the subject.

The present invention also provides a method of reducing an inflammatory response in a mammal the method comprising orally administering to the mammal a plant or a plant extract comprising an effective dose of a plant-derived mammalian contra-inflammatory cytokine. An example of an inflammatory response is inflammatory bowel disease, and an example of a contra-inflammatory cytokine is plant expressed IL-10.

Also according to the present invention, there is provided a method for the production of a protein of interest, the method comprising, i) selecting a low nicotine, low alkaloid tobacco plant;

ii) transforming the plant with a vector containing a gene encoding the protein of interest and operatively linked with 5' and 3' regulatory regions allowing expression of the protein of interest, thereby producing a transformed plant;

iii) growing and harvesting the transformed plant containing the protein of interest, and;

iv) obtaining plant tissues from the transformed plant that comprise the protein of interest.

Preferably the leaves of the low-nicotine, low-alkaloid tobacco plant comprise, a nicotine concentration (wt/wt) which is less than about 10%, more preferably less than about 5%, still more preferably less than about 2.6% the nicotine concentration (wt/wt) of Delgold tobacco plants grown under the same conditions, and an alkaloid concentration (wt/wt) which is less than about 10%, more preferably less than about 5%, still more preferably less than about 0.28%, the alkaloid concentration (wt/wt) of Delgold tobacco plants grown under the same conditions. The alkaloid may consist of, but is not limited to, nicotine, myosmine, anabasine and anatabine.

Also according to the present invention as defined above, the protein of interest may comprise, but is not limited to a cytokine, for example but not limited to a contra-inflammatory cytokine such as IL-4, IL-10 or a combination thereof, or the protein of interest may comprise an autoantigen, for example, but not limited to GAD, or a combination of an cytokine and an autoantigen, for example, but not limited to IL-4 and GAD.

Also according to the present invention, there is provided a plant or portion thereof comprising plant expressed IL-4 and GAD. Further contemplated is a composition comprising plant expressed IL-4 and GAD.

This invention embraces a method for the production of a protein of interest comprising, providing a low nicotine, low alkaloid tobacco plant containing a gene encoding the protein of interest and operatively linked with 5' and 3' regulatory regions, growing and allowing expression of the protein of interest. Further contemplated by the present invention is a method of producing a cytokine for oral administration comprising, i) transforming a plant, or portion thereof with a nucleotide sequence encoding the cytokine;

ii) expressing the cytokine in the plant, and;

iii) harvesting the plant or portion thereof.

Any cytokine may be produced by the plant, but it is preferably an interleukin. The interleukin may be selected from the group consisting of IL-1 to IL-24, IL-16, IL-27, or a combination thereof. Preferably the leaves of the low-nicotine, low-alkaloid tobacco plant comprise, a nicotine concentration (wt/wt) which is less than about 10%, more preferably less than about 5%, still more preferably less than about 2.6% the nicotine concentration (wt/wt) of Delgold tobacco plants grown under the same conditions, and an alkaloid concentration (wt/wt) which is less than about 10%, more preferably less than about 5%, still more preferably less than about 0.28% the alkaloid concentration (wt/wt) of Delgold tobacco plants grown under the same conditions. The alkaloid may consist of, but is not limited to, nicotine, myosmine, anabasine and anatabine.

The present invention further contemplates a plant produced according to the methods as defined above. For example, but not wishing to be limiting, the plant may be a potato, tomato, alfalfa, corn, tobacco, or a low-nicotine, low-alkaloid tobacco plant comprising a transgenic nucleotide sequence capable of producing one or more proteins of interest in the plant. In a embodiment of the present invention the protein of interest may comprise, but is not limited a cytokine, for example a contra-inflammatory (anti-inflammatory) cytokine, IL-4, IL-10, TGFβ, or an autoantigen, for example GAD, or a combination thereof. In a further aspect of an embodiment, the protein of interest comprises IL-4 and GAD. The present invention also contemplates plant cells, tissues, seeds comprising the protein or proteins of interest.

Also provided in the present invention is a method of delivering an interleukin, an autoantigen, or both an interleukin and an autoantigen to a subject in need thereof comprising, orally administering the plant as defined above, or portion thereof, to the subject.

The present invention also discloses a method of enhancing the effect of an immune response against an antigen in a subject, comprising administering a plant-expressed interleukin and the antigen to the subject.

This summary of the invention does not necessarily describe all necessary features of the invention, but that the invention may also reside in a sub-combination of the described features.

BRIEF DESCRIPTION OF THE DRAWINGS

These and other features of the invention will become more apparent from the following description in which reference is made to the appended drawings wherein:

FIG. 5A and FIG. 5B show the quantity of IL-10 secreted to the apoplast following transformation of tobacco plants with nucleotide sequences comprising either a long hIL-10 3'UTR region or a short hIL-10 UTR region respectively FIG. 5C shows the quantity of plant recombinant IL-10 expressed in transgenic tobacco plants transformed with an IL-10 nucleotide sequence which further comprises a KDEL endoplasmic reticulum retention signal.

FIG. 10 shows the oligonucleotide cassettes for integration of TMV 5'-untranslated region and PR-1b transit peptide sequences into transgene constructs. FIG. 10(A) the TMV leader sequence. FIG. 10(B) the PR-1b signal peptide sequence. FIG. 10(C) the amino acid translation of encoded signal peptide. Identity, sequence, and position of each oligonucleotide within the cassettes are indicated. TMV sequence is marked in bold, PR-1b signal peptide sequence in plain letters and additional sequence in italics. Nucleotides constituting all or part of the initiation codon are present within boxes. Oligonucleotides #1091 (SEQ ID NO:1); #1092 (SEQ ID NO:4); and #1093 (SEQ ID NO:2) represent the TMV oligo set. Oligonucleotides #1091, #1092 (SEQ ID NO:1 and 4), and #4361 through #4365 (SEQ ID NOs: 3, 5, 6, 8 and 9 respectively) represent the TMV-PR oligo set.

FIG. 14 shows the cDNA sequence of human IL-10. The cDNA sequence is denoted in small letters, the encoded protein sequence is denoted in capital letters below the nucleotide sequence with the one letter amino acid code. The signal peptide sequence is boxed and shaded. Oligonucleotides used to amplify hIL-10 sequences or to fuse other sequences to the hIL-10 gene are shown in capital letters underlined by an arrow. Restriction sites introduced by PCR are shaded. Encoded amino acids are shown above the hIL-10-His-KDEL oligonucleotide sequence.

FIG. 15(A) shows the full length, 1601 bp cDNA of IL-10. Transformed plants comprising this construct are designated as "F" plants in FIG. 16. FIG. 15(B) shows a truncated IL-10 sequence comprising nucleotides 4-732, with only a portion of the 3' UTR (168 bp) Transformed plants comprising this construct are designated as "E" plants in FIG. 16. FIG. 15(C) shows an IL-10 construct with the 3' UTR portion removed, and a thrombin recognition sequence, a His tag and a KDEL sequence added to the 3' end of the IL-10 sequence. The region containing the thrombin-His tag and KDEL sequence is magnified to show the order of those sequences with respect to the hIL-10 gene. Transformed plants comprising this construct are designated as "G" plants in FIG. 16. The hIL-10 coding region is depicted by a dark shaded box, the signal peptide is shown by a light shaded box, and the cDNA is shown by a straight line. Oligonucleotides are represented by short arrows.

Figure 1:
FIG. 1 shows an immunoblot of proteins extracted from leaf tissues of transgenic tobacco plants transformed with a plant expression vector comprising human GAD65. Lanes 1-2: protein extracts from individual transgenic lines (40 μg total protein was loaded onto the gel); Lane C: protein extracts from empty vector-transformed tobacco plants; rmGAD67: recombinant mouse GAD67 purified from *E. coli* (standard).

(81V9-10), chow plus 20% 81V9 (81V9-20), chow plus 10% G7-2-9 (IL10-10), or chow plus 20% G7-2-9 (IL10-20).

DESCRIPTION OF PREFERRED EMBODIMENT

The present invention relates to the use of plants as a bioreactor for the production of heterologous proteins. More specifically this invention relates to the expression of transgenes of interest for oral administration using plants.

The following description is of a preferred embodiment by way of example only and without limitation to the combination of features necessary for carrying the invention into effect.

According to an aspect of an embodiment of the present invention, there is provided a transgenic plant expressing one or more proteins of interest. The transgenic plant, or portion thereof expressing the one or more proteins of interest may be orally administered to a subject with minimal or no prior processing. In such an embodiment, which is not meant to be limiting in any manner, the plant or portion thereof comprising the one or more proteins of interest may be used to treat, prevent or both treat and prevent a medical ailment in a subject.

By "operatively linked" it is meant that the particular sequences interact either directly or indirectly to carry out their intended as described herein. The interaction of operatively linked sequences may for example be mediated by proteins that in turn interact with the sequences. A transcriptional regulatory region and a sequence of interest are "operably linked" when the sequences are functionally connected so as to permit transcription of the sequence of interest to be mediated or modulated by the transcriptional regulatory region.

By "DNA regulatory region" it is meant a nucleic acid sequence that has the property of controlling the expression of a DNA sequence that is operably linked with the regulatory region. Such regulatory regions may include promoter or enhancer regions, and other regulatory elements recognized by one of skill in the art. By "promoter" it is meant the nucleotide sequences at the 5' end of a coding region, or fragment thereof that contain all the signals essential for the initiation of transcription and for the regulation of the rate of transcription and include constitutive promoters, tissue specific promoters or inducible promoters as would be known to those of skill in the art. Examples of known constitutive regulatory elements include promoters associated with the CaMV 35S transcript. (Odell et al., 1985, *Nature*, 313: 810-812), the rice actin 1 (Zhang et al, 1991, *Plant Cell*, 3: 1155-1165) and inosephosphate isomerase 1 (Xu et al, 1994, *Plant Physiol.* 106: 459-467) genes, the maize ubiquitin 1 gene (Cornejo et al, 1993, *Plant Mol. Biol.* 29: 637-646), the *Arabidopsis* ubiquitin 1 and 6 genes (Holtorf et al, 1995, *Plant Mol. Biol.* 29: 637-646), and the tobacco translational initiation factor 4A gene (Mandel et al, 1995 *Plant Mol. Biol.* 29: 995-1004). The term "constitutive" as used herein does not necessarily indicate that a gene under control of the constitutive regulatory element is expressed at the same level in all cell types, but that the gene is expressed in a wide range of cell types even though variation in abundance is often observed.

By "protein of interest" it is meant any protein that is to be expressed in a transformed plant. Such proteins may include, but are not limited to, pharmaceutically active proteins, for example one or more than one of IL-1 to IL-24, IL-26 and IL-27, cytokines, contra-inflammatory cytokines, Erythropoietin (EPO), CSF, including G-CSF, GM-CSF, hPG-CSF, M-CSF, TGFβ, Factor VIII, Factor IX, tPA, hGH, receptors, receptor agonists, antibodies, neuropolypeptides, insulin, vaccines, growth factors for example but not limited to epidermal growth factor, keratinocyte growth factor, transformation growth factor, growth regulators, antigens, autoantigens including, but not limited to GAD, their derivatives and the like.

The one or more proteins of interest may be expressed within a plant using an appropriate vector comprising a nucleotide sequence that encodes a protein of interest, and that is capable of being expressed within plant tissue. Such a vector may also include ubiquitous or tissue specific promoters and other 5' and 3' regulatory elements as would be known to one of skilled in the art. Other elements that may be included with this vector include sequences for targeting the protein of interest to the cytosol or secretory pathway such as, but not limited to, the C-terminal KDEL sequence, an endoplasmic reticulum retention motif (Schouten et al 1966). Other retention signals, as would be known to one of skill in the art, may also be used for this purpose. Furthermore, such a vector may include marker genes for the detection of expression within the transgenic plant, or linker sequences, proteolytic cleavage sequences, and other sequences that aid in the purification of a protein of interest. An example, which is not to be considered limiting in any manner, of a sequence that aids in the purification of a protein of interest is an affinity tag, for example, sequences that encode a HIS tag. However, it is to be understood that other affinity tags, as are known within the art, may also be used for the purpose of purification. An example, of a sequence that aids in proteolytic cleavage may include, but is not limited to a thrombin cleavage sequence. Such a sequence may permit a protein of interest to be separated from an attached co-translated sequence, such as, but not limited to a KDEL or other sequence.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprises a plant or portion thereof which has not be subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like. Any plant may be used to express the protein described herein, for example but not limited to food-crop plants for example alfalfa, corn, wheat, soybean, potato, canola, and non food crop plants, such as tobacco or a low-nicotine, low alkaloid tobacco.

By the term "minimal processing" it is meant plant matter, for example, a plant or portion thereof comprising a protein of interest which is partially purified to yield a plant extract, homogenate, fraction of plant homogenate or the like. Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve methods such as those employed for the preparation of F1P as disclosed in Woodleif et al (1981). These methods include aqueous extraction of soluble protein from green tobacco leaves by precipitation with any suitable salt, for example but not limited to $KHSO_4$. Other methods may include large scale maceration and juice extraction in order to permit the direct use of the extract. As an example, which is not meant to be limiting in any manner, a composition comprising plant matter, IL-4, and GAD 65 proteins of interest may be partially purified to increase the yield of IL-4 and GAD in relation to the amount of plant matter.

By "oral administration" it is meant the oral delivery of plant matter to a subject in the form of plant material or tissue. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

By "medical ailment" it is meant a defined medical condition that can be treated with a specific pharmaceutical suitable for the treatment of the condition. Examples of such medical ailments and their corresponding suitable pharmaceutical include, but are not limited to: diabetes and the administration of IL-4 or insulin or a combination thereof; other autoimmune diseases for example rheumatoid arthritis, diabetes and the administration of a cytokine, for example IL10, IL-4, GAD, or a combination thereof, allergy treatment and administration of IL-12, or direct effects, for example, cytokines may also be used for topical delivery in the treatment of psoriasis or for wound healing, for the treatment of liver fibrosis or chronic hepatitis C and treatment using IL-10, for conditions related to blood clotting with the administration of Factor VIII, Factor IX or tPA or combinations thereof; medical conditions requiring stimulation of progenitor cells to monocytes/macrophages and the administration of G-CSF, GM-CSF, hPG-CSF, M-CSF or combinations thereof; viral infections and the administration of interferons e.g. interferon-α, interferon-β, interferon-γ or combinations thereof.

In an aspect of an embodiment of the present invention, the proteins of interest comprise one or more cytokines, for example contra-inflammatory cytokines or interleukins, and one or more autoantigens. By the term "autoantigen" it is meant a compound, such as but not limited to, a protein of interest that is administered to a subject that otherwise produces this protein and this exogenously administered protein is capable of eliciting an immunological response following oral administration. Preferably, the immunological response comprises either reducing or eliminating T lymphocytes and other cells capable of tissue specific injury, or inducing regulatory T lymphocytes or other cells which may lead to reduced destruction of tissues expressing the autoantigen either by direct effect or by secondary effect on destructive T lymphocytes or other cells. As examples, which are not meant to be limiting in any manner, the present invention provides a transgenic plant expressing, IL-4, IL-10, or IL-4 and glutamic acid decarboxylase (GAD).

Any cytokine, for example a contra-inflammatory cytokine, interleukin, or biologically active derivative or variant thereof, and any autoantigen, or biologically active derivative or variant thereof may be produced in the transgenic plant of the present invention. The cytokine and autoantigen may comprise amino acid sequences which are found naturally in the same or different species. Further, the cytokine may be produced in the same plant cells, or tissues, as the autoantigen, or the cytokine and autoantigen may be produced in different plant cells or tissues of the same plant. Similarly, the one or proteins of interest may be expressed under the control of different regulatory regions that are active at different stages of the cell cycles, plant or tissue development. Without wishing to be considered limiting in any manner the plant may express murine IL-4 and murine GAD 67; murine IL-4 and murine GAD 65; murine IL-4 and human GAD 65; murine IL-4 and human GAD 67; human IL-4 and human GAD 65; and human IL-4 and human GAD 67.

The present invention further contemplates a composition comprising a plant-expressed cytokine, for example a contra-inflammatory cytokine, an autoantigen, or a plant expressed cytokine and autoantigen. In an aspect of an embodiment of the present invention, which is not meant to be considered limiting in any manner, the composition may comprise plant-expressed IL-10, plant expressed IL-4, plant expressed GAD, or plant expressed IL-4 and GAD The IL-10, IL-4, and GAD may comprise an amino acid sequence which is identical to any IL-10, IL-4, and GAD amino acid sequence, respectively, as known in the art. Further, the invention contemplates variations and derivatives of IL-10, IL-4 and GAD which comprise biological activity. The IL-10, IL-4, and GAD may be produced together in a single plant or they may be produced in separate plants.

For example the composition of the present invention may comprise a combination of autoantigen such as GAD from one plant, combined with a plant expressed adjuvant cytokine such as IL-4, or IL-10 from a second plant. Production of these proteins in separate plants allows control of the composition mix in terms of relative proportions of autoantigen to cytokine. For example, which is not to be considered limiting, the composition of the present invention may comprise a combination of partially purified IL-4 from a first plant and GAD from a second plant comprising associated plant matter, or the composition may comprise IL-4 and GAD obtained from separate plants following purification of these proteins.

Alternatively, the expression vector used for the transgenic plants may comprise nucleic acid sequences that express both the autoantigen or transplantation antigen, and a cytokine or a number of cytokines. Such a vector may be used to develop a single plant expressing several proteins of interest. Similarly, a plant expressing the autoantigen or transplant antigen may be crossed using techniques as known in the art, with a plant expressing one or more than one cytokines in order to produce a plant expressing both an autoantigen or transplant antigen and one or more than one cytokines However, plants may also be useful in oral application to the gut for modulation of immune responses in the absence of a concurrently administered autoantigen. An example of such a case, where an autoantigen may not be required relates to inflammation, for example but not limited to inflammatory bowel disease (IBD), by which the direct topical application to the gut of anti-inflammatory cytokines may be used to prevent and treat disease. Cytokines such as interleukin-10 and interleukin-4 may be used for this purpose, however, other cytokines and growth factors growth factors which have a direct protective effect on enterocyte epithelial cell survival in any inflammatory condition as would be determined by one of skill in the art may also be used.

The present invention provides a composition comprising a cytokine or growth factor, an autoantigen or transplantation antigen, or a combination thereof. This composition may be used for a variety of purposes, for example but not limited to, augment the tolerizing capacity of an autoantigen, either to improve the tolerance effect of low level expression of autoantigen, or to maximize the effect by inducing regulatory cells or deleting harmful cells, or by benefiting oral tolerance by skewing immune responses at the time of antigen presentation. The composition may also be used to deliver cytokines, growth factors or other compounds expressed within the plant delivery system to attenuate or abrogate inflammatory conditions as would be found in inflammatory bowel disease but also graft-versus-host disease following transplantation, or as a result of inflammation secondary to injury caused by infection or physical injury of epithelial and other parenchymal cells of the gut or skin.

Without wishing to be bound by theory, the use of endogenous proteins such as cytokines as adjuvants may augment oral immune tolerance by skewing T helper responses to a less harmful subset however, these proteins would not induce neutralizing immune responses since they are endogenous proteins. Neutralizing immune responses may be observed with the use of foreign proteins, for example, mucosal immune adjuvants such as cholera toxin B subunits (Arakawa T, et al., 1998, Nat Biotechnol. 16:934-8), where with continued exposure, immune responses and antibodies will be directed against the cholera toxin B subunits and lead to neutralization of any beneficial effect thus preventing long term oral tolerance induction.

The immune response at the time of initial antigen presentation to T lymphocytes is influenced by the presence of cytokines which act as potent biological response modifiers at the time of initial activation. Cytokines such as IL-4 and IL-10 may shift T cell responses towards T helper 2 (Th2) subsets, which have been shown to be of benefit in autoimmune diseases mediated by autoaggressive Th-1 helper (Th1) subsets. Alternatively, Th-1 cytokines (eg. interferon gamma, IL-2, IL-12) might skew the T helper subset to Th-1 responses, and increase responses which may be useful to augment endogenous protective responses to pathogens for example, within the gut and skin. Therefore, the present invention provides plant(s) expressing both regulatory cytokines and an autoantigen(s) or transplantation antigen(s) of interest, as these compositions would maximize the effect of antigen specific oral immune tolerance.

The use of plants as an expression system for the production of mammalian antigen proteins offers unique advantages beyond high production yields at competitive low cost. Immune tolerance requires activation events within T lymphocytes, and plants which includes lectins, in addition to other compounds, may facilitate such activation events. While the specificity of oral immune tolerance depends on antigen selection, the magnitude of response is influenced by expression levels of the transgenic protein of interest within plants. It can also be influenced by the presence of immune adjuvants or response modifiers present within the composition. Plant lectins for example expressed within the cell walls of plant cells may generally augment the immune response by direct activation of T cells. Additionally, the accumulation of transgenic proteins within plant cell compartments may become protected from degradation in the digestive tract (Kong et al, 2001, P.N.A.S 98:11539-11544). This would augment oral immune tolerance by delivering transgenic plant protein to immune effector sites more in the gut distal to the digestive environment of the stomach and duodenum.

Furthermore, plants may also be useful for direct, oral application of a cytokine to the gut for modulation of immune responses in the absence of a concurrently administered autoantigen, for example as in the cases of inflammation such as in the case of inflammatory bowel disease (IBD). In this example, the direct topical application to the gut of anti-inflammatory cytokines would prevent and treat disease. This approach would include the use of cytokines such as IL-10 and IL-4 but may also include other cytokines and growth factors, or growth factors which have a direct protective effect on enterocyte epithelial cell survival in any inflammatory condition.

Inflammatory bowel disease (IBD) represents a spectrum of diseases with over-lapping clinical presentations, although ulcerative colitis and Crohn's colitis, the most widely represented and serious IBD in North America have characteristic features that aid diagnosis. Treatments currently used are often inadequate, poorly tolerated, associated with serious adverse effects and expensive. It is known that the human contra-inflammatory cytokine interleukin-10 (IL10) may have application in the treatment of inflammatory bowel disease (Leach et al. 1999. Tox. Path. 27:123-133). IL-10 given systemically has been shown to be of benefit in rodent models of inflammatory bowel disease, a similar but less modest effect was also observed in human clinical trials (Fedorak et al. 2000. Gastroent. 119:1473-1482; Schreiber et al. Gastroent. 119:1461-1472). The magnitude of the therapeutic benefit in humans was limited by systemic toxicity as patients treated with higher amounts of IL-10 demonstrated a reduction in both hemoglobin and platelet levels. Without wishing to be bound by theory, direct application of cytokines through oral administration of plant material expressing cytokines may avoid this systemic effect in a manner similar to that observed with the topical application of drugs.

One new method demonstrated in animal models of Crohn's disease was intra-gastric inoculation of an animal model of Crohn's disease with genetically engineered Lactococci that secrete recombinant IL10 (Steidler et al. Science. 289:1352-1355). The treatment was effective in the test animals, although its application in humans may be limited because of the containment problems that would result from the presence of heavy loads of genetically engineered bacteria in human faeces. Oral administration of recombinant cytokines has been suggested and may be a possibility for IL10 (Rollwagen and Baqar 1996. Immunol. Today 17:548). Although there are concerns about digestive degradation of oral cytokines, there is evidence that IL10 is biologically active at mucosal surfaces, at least when administered with an autoantigen and when related to oral tolerance (Slavin et al. 2001. Int. Immunol. 13:825-833). The problem that remains is the delivery of a sufficient dose of recombinant IL10 to lesions in the GI tract so that a direct contra-inflammatory effect is created.

Crohn's disease is a chronic inflammatory bowel disease with frequent remissions and exacerbations, and several extra-GI manifestations. Lesions are typically discontinuous and can occur anywhere within the GI tract. The most common locations are ileum and colon, and formation of structures and fistulas are common. In contrast, ulcerative colitis is contiguous and characteristically affects the colon.

While the etiology of both these inflammatory bowel diseases remain unknown, there is data demonstrating the participation of immune cells in these conditions. Cytokines may direct the intensity, extent, and eventual outcome of inflammatory lesions. Interestingly, mice made deficient for IL-10, by targeted gene disruption, develop bowel inflammation and lesions resembling inflammatory bowel disease, which can be improved by systemic administration of IL-10 (Kuhn et al. 1993). The balance between proinflammatory cytokines such as interleukin-1, interleukin-6, γ-interferon and tumor necrosis factor (TNF) and anti-inflammatory cytokines such as receptor antagonists, IL-10, IL-4, and transforming growth factor beta (TGF-β) might ultimately determine the outcome of inflammatory bowel disease (Fiocchi 1993). By its nature in down regulating pro-inflammatory cytokines, for example TNF-α and up regulation of interleukin-1 receptor antagonists, IL-10 may be an effective strategy to treat inflammatory bowel disease. The present treatments for inflammatory bowel disease are empirically designed to reduce inflammation and rely heavily on corticosteroids and immuno-solisolates (5-ASA).

Human IL-10 has been cloned, and both mouse and human cDNA encode functionally and structurally similar proteins (with 178 amino acids) including a hydrophobic leader sequence and greater than 70% homology in predicted amino acid sequences. Interleukin-10 (IL-10) exists in both monomeric and homodimeric forms. Biological activity is known to be associated predominantly with the homodimeric form of IL-10.

In addition to production by CD4+ TH-2 clones, IL-10 is produced by B cells, activated mast cells, macrophages, monocytes and keratinocytes. There are multiple roles for IL-10 in the regulation of the immune response, including inhibition of T cell, monocyte and macrophage function, as well as inhibition of cytokines particularly those of the TH-1 T cell subset (interferon gamma) and inhibition of B cell proliferation. The inhibition of various cytokines such as interferon gamma, GM-CSF and TNF following lectin or anti-CD3 activation is both transcriptional and translational. There is also inhibitory activity on MHC class 11 antigen expression, which is a protein central to the recognition of antigen presenting cells by T-cell. IL-10 also inhibits the production of hydrogen peroxide and nitric oxide following interferon-gamma activation. Therefore there is a strong basis for the concept that IL-10 naturally occurs to provide negative regulation to immune responses.

Glutamic acid decarboxylase (GAD), is an enzyme which is found in brain as well as pancreatic islets. There are several isoforms including GAD65 (molecular weight of 65 kDa) and GAD67 (molecular weight of 67 kDa), which are differentially expressed in various species, within pancreatic islets. Both isoforms are implicated in the pathogenesis of IDDM, as immune responses to GAD appear prior to the onset of clinical disease, and strategies used to re-establish tolerance to both isoforms of GAD prevent disease in mammals, for example mice. Fragments of GAD are also known to and assist in oral tolerance (see for example: U.S. Pat. Nos. 5,837,812; 6,211,352; WO 96/26218; U.S. Pat. Nos. 5,645,998; 5,762,937; 6,001,360; 5,475,086; 5,674,978; 5,705,626; 5,846,740; 5,998,366; 6,011,139; all of which are incorporated herein by reference), The immune response at the time of initial antigen presentation to T lymphocytes is influenced by the presence of cytokines which act as potent biological response modifiers at the time of initial activation. Without wishing to be bound by theory, contra inflammatory cytokines, for example but not limited to IL-4, IL-10, or TGF-β may shift T cell responses towards T helper 2 (Th2) subsets, which have been shown to be of benefit in autoimmune diseases mediated by autoaggressive Th-1 helper (Th1) subsets. Alternatively, Th-1 cytokines (eg. interferon gamma, IL-2, interleukin-12) might skew the T helper subset to Th-1 responses, and increase responses which may be useful to augment endogenous protective responses to pathogens for example, within the gut and skin. Therefore plant(s) expressing both regulatory cytokines and an autoantigen(s) or transplantation antigen(s) of interest, would maximize the effect of antigen specific oral immune tolerance.

IL-4 is a growth and differentiation factor for T-cells. In particular, IL-4 promotes the development of the subset of T helper (Th2) cells from native T cells upon antigen simulation. IL-4 producing Th2 cells generally protect against the onset of many organ-specific autoimmune diseases, including type 1 diabetes. Thus the availability of an abundant source of IL-4 may prove invaluable for the immunotherapy of diabetes.

Figure 3:
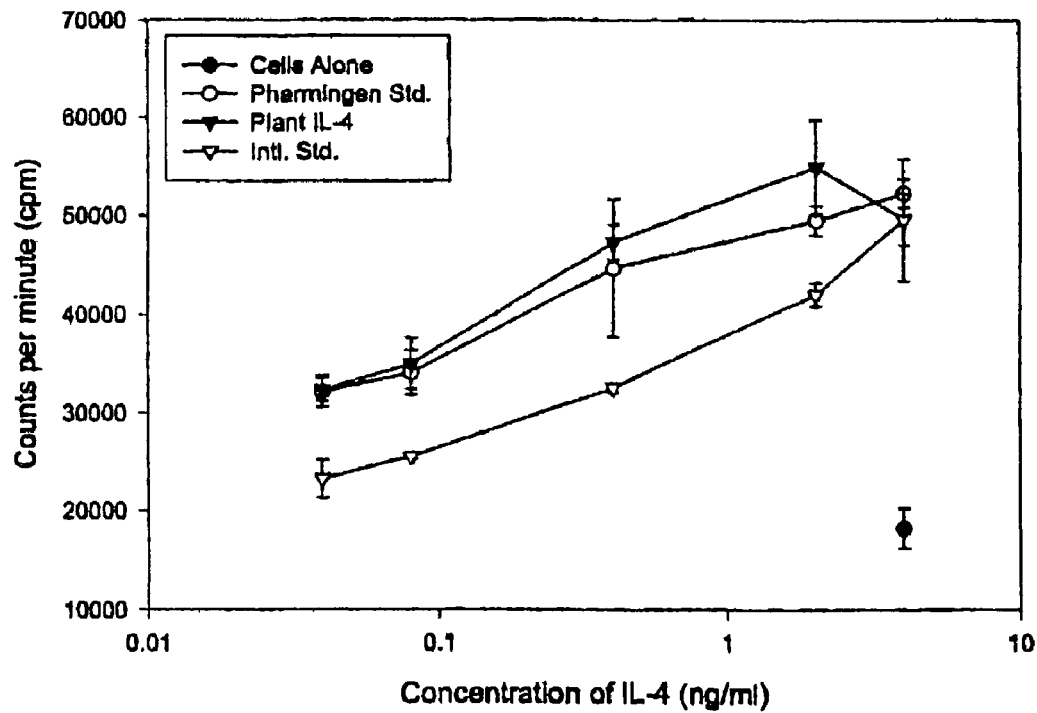
FIG. 3 shows results of an MC/9 cell proliferation assay exhibiting the biological activity of plant-derived IL-4. The black circle indicates the background level of $^3$H incorporation by MC/9 cells. Black triangles represent plant recombinant IL-4, clear circles represent recombinant IL-4 obtained from Pharmingen, and open triangles represent the international IL-4 reference obtained from the National Cancer Institute-Frederick Cancer Research and Development Center
Figure 8:
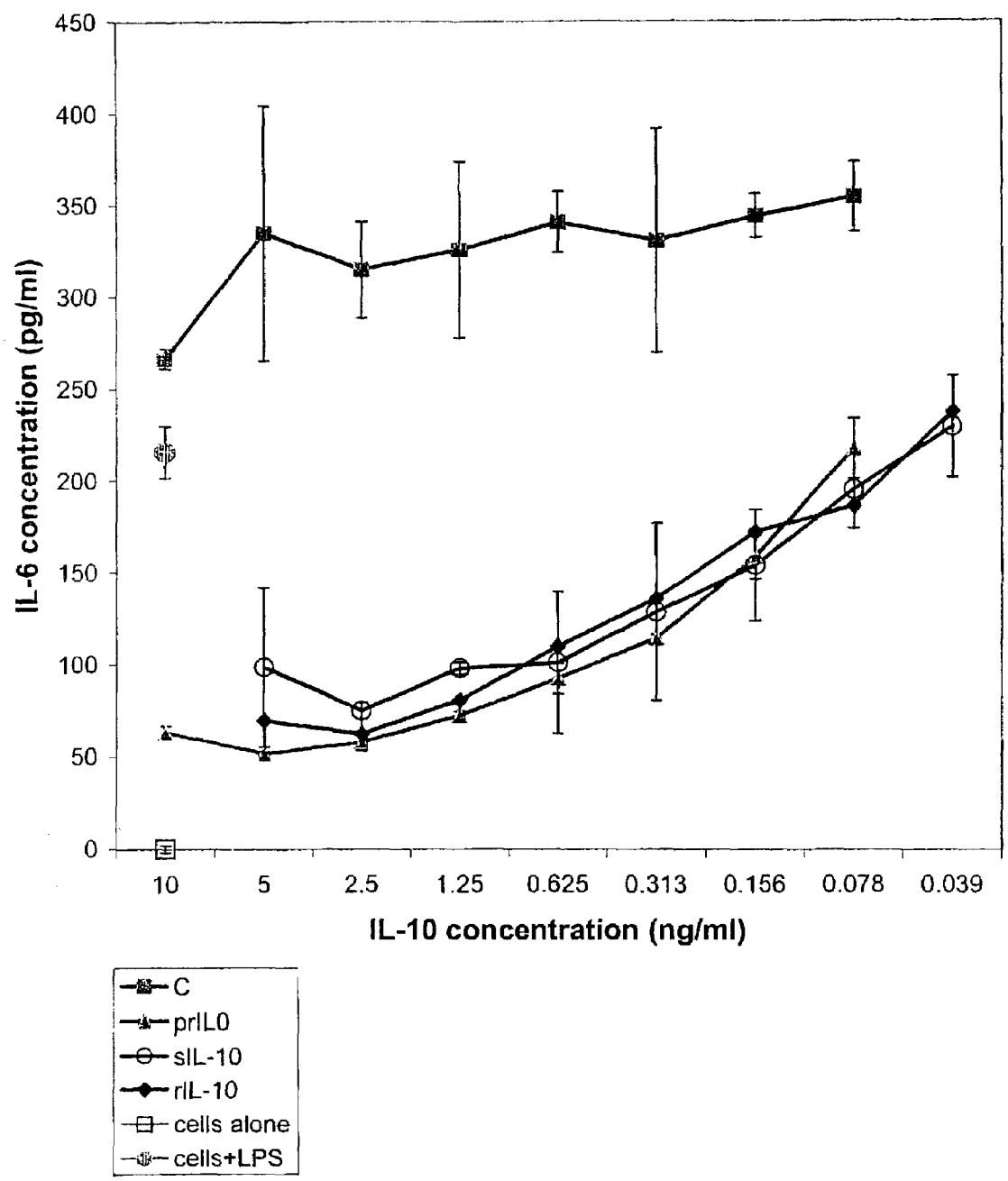
FIG. 8 shows results of biological activity determination of prIL-10, hIL-10 and prIL-10 inhibited LPS-induced secretion of IL-6 by macrophage/monocyte PU5-1.8 cells. $4 \times 10^5$ LPS-stimulated cells/ml were incubated with increasing concentrations of prIL-10 (plant produced), rIL-10 (insect produced) or sIL-10 (reference standard) for 24 h. Cell culture supernatants were collected and tested for IL-6 concentrations by ELISA. Vertical lines indicate standard error bars. Gray triangles indicate plant recombinant IL-10 (prIL-10), gray squares are control plant extract (C), open circles are the reference IL-10 standard, black diamonds are recombinant IL-10 (rIL-10, from insect), the open square represents unstimulated cells, and the gray circle represents LPS-stimulated cells.

Plant produced IL-4 is biologically active, for example as demonstrated by the stimulation of mast cell growth in the presence of IL-4 (FIG. 3). In this example, plant recombinant IL-4 exhibits the same effect as commercially available IL-4, and IL-4 from other sources. Similarly, plant produced IL-10 is also biologically active, for example as demonstrated in the inhibition of LPS-induced secretion of IL-6 by macrophage/monocyte cells (FIG. 8). This example demonstrates that plant recombinant IL-10 exhibits the same biological activity as recombinant insect IL-10, or IL-10 from other sources.

Therefore, the present invention provides is a method of producing a cytokine within a plant for oral administration comprising, i) providing, or transforming, a plant, or portion thereof with a nucleotide sequence encoding said cytokine;

ii) expressing the cytokine in the plant, and if desired;

iii) harvesting the plant or portion thereof.

Any cytokine may be produced in the plant including growth factors, but the cytokine is preferably an interleukin. If the cytokine is an interleukin, then the interleukin may be selected from the group consisting of IL-1 to IL-24, IL-26, IL-27 and growth factors, or a combination thereof. Example of growth factors include but not limited to epidermal growth factor, keratinocyte growth factor, erythropoietin and transformation growth factor.

The steps of transforming and expressing may be performed in any manner as described within the art and may be readily practised by a person of skill in the art. For example, the constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology,* Academy Press, New York VIII, pp. 421-463 (1988); Geierson and Corey, *Plant Molecular Biology,* 2d Ed. (1988); and Miki and Iyer, *Fundamentals of Gene Transfer in Plants.* In *Plant Metabolism,* 2d Ed. D T. Dennis, D H Turpin, D D Lefebrve, D B Layzell (eds), Addison Wesly, Langmans Ltd. London, pp. 561-579 (1997).

Furthermore, the plant may be any plant known in the art, for example, but not limited to a tobacco plant. If the plant is a tobacco plant, it is preferred that the tobacco plant is a low-nicotine, low alkaloid tobacco plant.

Following the step of harvesting, the plant, or portion thereof, may be orally administered to a subject, or the plant, or portion thereof, may be partially purified as described previously prior to being administered to a subject.

The present invention provides a method of treating, or preventing diabetes in a subject. The method comprises administering to a subject a plant or more than one plant expressing an autoantigen, for example GAD, with a cytokine, for example IL-4 or IL-10, either singly or in combination, to augment oral immune tolerance to the autoantigen. Any IL-4, IL-10, or GAD may be used provided that the protein exhibits IL-4, IL-10 or GAD activity, respectively. However, it is well known in the art that fragments of GAD are biologically active, or that fragments of GAD assist in oral tolerance (see for example: U.S. Pat. Nos. 5,837,812; 6,211,352; WO 96/26218; U.S. Pat. Nos. 5,645,998; 5,762,937; 6,001,360; 5,475,086; 5,674,978; 5,705,626; 5,846,740; 5,998,366; 6,011,139; all of which are incorporated herein by reference), therefore the present invention also pertains to a method of treating, or preventing diabetes in a subject comprising administering to a subject a plant, or more than one plant, expressing an autoantigen, for example GAD or a fragment thereof, with a cytokine, for example IL-4 or IL-10, either singly or in combination.

Preferably the IL-4, IL-10, GAD, or a fragment of GAD, comprise amino acid sequences which are substantially identical to the amino acid sequences of the proteins in the subject being treated. By substantially identical it is meant that the administered amino acids sequences exhibit from about 95% to about 100% identity with the subject sequence. Preferably, the administered sequence exhibits 100% identity with the subject sequence. Thus, as will be evident to someone of skill in the art, preferably a human IL-4 is employed with human GAD to treat, prevent or both treat and prevent diabetes in a human subject.

Homology determinations may be made as known in the art using oligonucleotide alignment algorithms for example, but not limited to a BLAST (GenBank URL: www.ncbi.nlm.nih.gov/cgi-bin/BLAST/, using default parameters: Program: blastp; Database: nr; Expect 10; filter: default; Alignment: pairwise; Query genetic Codes: Standard(1)) or FASTA, again using default parameters.

The present invention provides a vector comprising a nucleotide sequence encoding an cytokine, a autoantigen or both a cytokine and an autoantigen, and operatively linked with one, or more than one regulatory regions active in a plant. An example of the cytokine is an interleukin, for example any one of IL1 to IL24, IL-26 or IL-27, or a contra-inflammatory cytokine, for example but not limited to IL-4, IL-10 or TGF-β. Preferably, the interleukin is a member of the IL-10 family (Fickensher, 2002, Trends in Immunology 23: 89), which includes members that have conserved helical structures of a homo-dimer, but variable receptor binding residues which alter their function. Examples of members of the IL-10 family include IL-10, IL-19, IL-20, IL-22, IL-24 and IL-26. More preferably the interleukin is IL-4 or IL10. An example of the autoantigen is GAD, or a fragment of GAD that is biologically active, or functional in assisting oral tolerance. The vector may further comprise a second nucleotide sequence fused to nucleotide sequence, the second nucleotide sequence encoding, an enzyme cleavage site, an endoplasmic reticulum retention signal, an affinity tag to aid purification of said protein of interest, or a combination thereof. Preferably the endoplasmic reticulum retention signal comprises the amino acid sequence KDEL. The present invention is also directed to a plant comprising the vector, and to plants expressing the nucleotide sequence as defined above.

Therefore, the present invention also provides a composition comprising a plant-expressed cytokine, and an autoantigen. Preferably the plant-expressed cytokine is a contra-inflammatory cytokine. More preferably, the contra-inflammatory cytokine, is IL-4. Furthermore, it is preferred that the autoantigen, is GAD, or a fragment thereof.

The present invention also provides a method of eliciting an immune response against an antigen in a subject, the method comprising orally administering a plant or portion thereof comprising an antigen and an interleukin to the subject. The antigen may be an autoantigen, for example, but not limited to GAD, or a fragment thereof. However, other autoantigens are also contemplated. Further, the interleukin may comprise IL-4, but may be one or more other interleukins. In an embodiment which is not meant to be limiting in any manner, the autoantigen is GAD, or a fragment thereof, and the interleukin is IL-4. Preferably the autoantigen and interleukin comprise sequences which are naturally present in the subject.

The present invention further contemplates a method of treating inflammatory bowel disease in a subject, the method comprising, administering a plant, or portion thereof comprising IL-10 to said subject. The inflammatory bowel disease may comprise ulcerative colitis or Crohn's colitis, but is not limited to these inflammatory bowel diseases.

Referring now to FIG. 1, there is shown an immunoblot of *Nicotiana tabacum* cv. SR1 tobacco plants transformed with a plant expression vector comprising the human GAD65 gene. The results show that transgenic plants producing human GAD65 exhibit a single protein band that is of the correct size. Further, the expression level of GAD65, estimated from blot densitometry was about 0.04% by weight of the total soluble protein. However, the level of expression maybe modulated in plants as would be evident to someone of skill in the art, for example, but not limited to, through the use of promoters with different activities, or by other accessory nucleotide sequences such as but not limited to enhancer, repressor, ER retention, and signal, sequences.

SR1 tobacco is provided as a non-limiting example of a plant that can be used to express a protein of interest as described herein, for example but not limited to GAD65. SR1 is a wild type tobacco plant with respect to nicotine expression, however, GAD65, and other proteins as described herein may be expressed in low nicotine tobacco as described below. The use of low nicotine tobacco may be desired if plant matter expressing one or more than one proteins described herein is to be orally administered.

Figure 2:
FIG. 2 shows an immunoblot of proteins extracted from leaf tissues of transgenic tobacco plants transformed with a plant expression vector comprising mouse IL-4. Lane 1: Standard mouse IL-4 (PharMingen); Lane 2: protein from empty vector-transformed tobacco plants; Lane 3: protein from IL-4 transgenic tobacco plants (40 μg protein was loaded per lane onto the gel).

Referring now to FIG. 2, there is shown an immunoblot of proteins extracted from *Nicotiana tabacum* cv. SR1) transformed with expression vectors comprising a nucleotide sequence encoding IL-4. The results indicate that transgenic IL-4 may be produced in plants. The immunoblot analysis exhibits a unique protein band recognized by a monoclonal antibody specific for mouse IL-4 which is comparable in size to standard recombinant mouse IL-4. Further, the expression level of plant-derived recombinant murine IL-4 (mIL-4), as determined by IL-4-specific ELISA, was found to be about 0.02% by weight of the total leaf protein. However, the level of expression may be modulated in plants as would be evident to someone of skill in the art, for example, but not limited to, through the use of promoters with different activities, or by other accessory nucleotide sequences such as, but not limited to enhancer, repressor ER retention, and signal sequences.

Referring now to FIG. 3, there is shown results following stimulation of a mast cell line with plant recombinant IL-4.

As shown in FIG. 3, proliferation of mast cells occurred with plant recombinant IL-4 demonstrating that plant-derived recombinant IL-4 is biologically active, and that it may be used as an immunomodulator in oral tolerance.

Transgenic tobacco leaf tissues comprising GAD and IL-4 were added to the feed of non-obese diabetic (NOD) mice in an amount of up to about 12% (w/w) of their diet. The amount of IL-4 was estimated to be about 10 μg to about 12 μg per mouse daily, whereas the amount of human GAD65 was estimated to be about 8 μg to about 10 μg per mouse daily. NOD mice receiving a composition of GAD65 and IL-4 produced within tobacco, exhibited a decrease in the incidence of developing diabetes compared with mice fed plant-produced GAD65, plant-produced IL-4, or plant matter comprising an empty vector. These results are described further in Example 6. The addition of GAD with IL-4 reduced the incidence of diabetes and as well reduced the severity of insulitus. However, also of clinical significance is the prevention of diabetes, as in the case of inducing protection with regulatory cells. Insulitus may still be a prominent feature in protected mice. Therefore the invention as described does not depend on the reduction of peri-islet infiltrates, as these infiltrates if present may not be destructive, and may represent T cells producing Th2 cytokines themselves.

IL-4 is known to mediate immunoglobulin class switching to IgE production (Ryan, 1997), and such an event is thought to be associated with the induction of an allergic response. As described in Example 6, oral immune tolerance with Th2 response skewing did not induce IgE response in the mouse models tested, either with autoantigen GAD or with IL-4.

Figure 4:
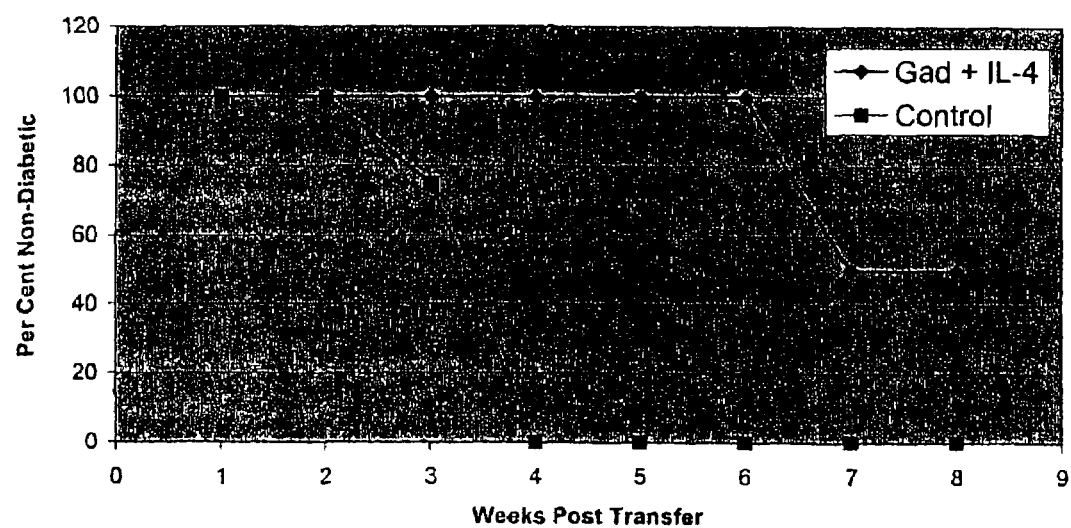
FIG. 4 shows development of diabetes in NOD-scid mice receiving a single i.v. injection of $10 \times 10^6$ spleen cells from diabetic donors mixed with $10 \times 10^6$ spleen cells from non-diabetic NOD mice fed transgenic GAD and IL-4 plants, in comparison to control mice receiving a single i.v. injection of $10 \times 10^6$ spleen cells from diabetic donors. Splenic mononuclear cells from mice fed GAD plus IL-4 plants were cotransferred with T cells from diabetic NOD mice to 8-week-old NOD-skid mice. A positive control group received cells only from diabetic NOD mice.

To examine whether the protection from diabetes in NOD mice fed both GAD and IL-4 transgenic plants may be associated with the induction of GAD-specific regulatory T cells, the ability of T cells from treated mice to inhibit the adoptive transfer of diabetes was tested. As shown in FIG. 4, 50% of the mice receiving a mixture of splenic mononuclear cells from GAD+IL-4 treated, diabetic mice developed diabetes (IDDM) at the end of 8 weeks post transfer, while 100% of the mice receiving only diabetic splenic cells developed IDDM. These data demonstrate that regulatory cells are only increased in those mice in which GAD and IL-4 are used concurrently. These regulatory cells can prevent the full diabetogenic effect of spleen cells taken from mice with new onset diabetes. These results also suggest that oral administration of plant produced GAD with interleukin-4 or other cytokines could possibly induce regulatory T cells in those not yet having overt diabetes, and in this pre-diabetic condition, regulatory cells may prevent the full onset of disease by blocking an activated effector T cell population. The delivery of GAD with IL-4 or other cytokines may also lead to protection by deletional mechanisms, with removal of autoreactive T cells, along with increased expression of regulatory T cells.

Thus, the present invention contemplates a method for inducing regulatory T-cells against an autoantigen in a subject, comprising orally administering a composition comprising IL-4 and an autoantigen. Further, there is provided a method of inducing regulatory T-cells against GAD in a subject, comprising orally administering a plant comprising IL-4 and GAD, or a composition comprising plant produced IL-4 and GAD. The subject may be any mammalian subject but is preferably human. In the latter embodiment, preferably the IL-4 is human IL-4, and GAD is human GAD 67, GAD 65, or a combination thereof.

The present invention also provides a plant or portion thereof expressing IL-4, IL-10, GAD, or a combination thereof. The plant may be any plant known in the art for example but not limited to, alfalfa, wheat, corn, soybean, canola, potato and tobacco. If the plant is a tobacco plant, it is preferred that the tobacco plant is a low-alkaloid plant, or a low-nicotine tobacco plant. More preferably, the plant is a low nicotine low alkaloid tobacco plant, such as, but not limited to, 81V-9 or SR1. A low nicotine low alkaloid tobacco plant is an example of a non-food crop plant.

From both a regulatory and public safety stand point non-food crop plants are ideal species for the transgenic production of biologically active proteins since the risk of leakage of transgenic plant material into the human food chain is negligible. Even though non-food crop plants are ideal species for use as bioreactors from both a regulatory and public safety point of view, there are several obstacles that must be overcome prior to their use as bioreactors.

A potential drawback with the use of non-food crop plants, for example tobacco, as bioreactors is that these plants may contain undesirable secondary plant products. Secondary plant products are constituents that are generally toxic or reduce the palatability of the plant tissue or that are addictive in nature. This is a significant concern since one of the benefits of preparing proteins of interest within a plant is that large quantities of protein may be required for administration (Ma and Hein, 1995). Therefore, any toxic, addictive, or otherwise non-desirable products should be avoided within the plant tissue. For example, tobacco plants contain high levels of secondary plant products such as nicotine and related alkaloids, making the plant tissue generally unsuitable for the direct oral administration. Earlier studies have described the administration of tobacco-derived proteins to mice, however, the proteins were in a partially purified form. For example, the study by Mason et al (1996) involved the direct oral administration of viral antigens expressed in potato tuber and tobacco. The potato tuber samples were directly fed to mice, yet the antigen, when obtained from tobacco, had to be partially purified using sucrose gradients prior to administration to mice. It is desirable to prepare transgenic proteins within non-food crop plants that permit the direct use of plant tissue for oral administration, or following minimal processing.

By "non-food crop plant" it is meant a plant that has traditionally not been used, or grown for human food purposes. Examples of non-food crop plants include, but are not limited to, ornamental plants, tobacco, hemps, weeds, trees and the like. It is contemplated that such non-food crops plants may be used for the production of one or more proteins of interest. In order that the non-food crop plant be used as a bioreactor for the production of one or more transgenically-expressed proteins of interest suitable for oral administration with minimal or no processing, it is preferably that such a non-food crop plant is characterized as being:

a) non-toxic;
b) palatable following minimal or no processing; and
c) characterized as having low levels of non-desirable secondary plant products such as alkaloids, nicotine, or the like.

However, if it is desired that the protein of interest is not to be orally administered, then any plant may be used for the production of a protein of interest, following the methods of the present invention, as described herein. In such applications where there is no need for orally administering the protein of interest, the protein of interest may be combined with other nucleic acid sequences that are useful for the purification of the protein of interest in order that the protein be suitable for further use.

Use of the terms "low nicotine" and "low alkaloid" with reference to plants, such as, but not limited to tobacco, means a plant that contains a significantly lower concentration of alkaloids when compared with a similar plant comprising regular alkaloid content. For example, which is not to be considered limiting in any manner, a low alkaloid tobacco plant may be defined as a plant that contains less than from about 0.2% to about 70% of the total alkaloids present in plants comprising a regular level of alkaloids. More preferably, a low-alkaloid plant is one that contains about 0.2% to about 10% of the total alkaloids present in plants comprising a regular level of alkaloids. An example of a low alkaloid plant, that comprises about 2.8% of the total alkaloid level of a regular tobacco, is 81V-9 (see Table 1, Example 4). Similarly, a low nicotine tobacco plant is one that contains a significantly lower concentration of nicotine when compared with a similar plant comprising regular nicotine content. For example, which is not to be considered limiting in any manner, a low nicotine tobacco plant may be defined as a plant that contains less than from about 0.2% to about 70% of the total nicotine present in plants comprising a regular level of nicotine. More preferably a low-nicotine plant is one that contains from about 0.2% to about 10% of the total nicotine present in plants comprising a regular level of nicotine. An example of a low nicotine plant, that comprises about 2.6% of the total nicotine level of regular tobacco, is 81V-9 (Table 1, Example 4). Conversely, an example of a tobacco plant which may be considered to comprise a regular level of alkaloids and nicotine is Delgold tobacco plants.

Low alkaloid or low nicotine plants may be obtained through conventional breeding programs (e.g. Chaplin, 1977), through selective down regulation of undesired genes (e.g. U.S. Pat. No. 5,260,205, issued Nov. 9, 1993 and U.S. Pat. No. 5,369,023, issued Nov. 29, 1994; inventors Nakatani and Malik), or by any other means e.g. mutagenesis followed by selection of desired traits. However, as is known to one of skill in the art, the ultimate nicotine or alkaloid level may still depend upon the environment under which the plant is grown.

Several methods have been proposed for the removal of nicotine from tobacco, however, these processes typically involve the treatment of post harvest-tissue. For example the use of solvents (EP 10,665, published May 14, 1980; inventors Kurzhalz and Hubert), or potassium metabisulphite, potassium sulphate and nitrate (U.S. Pat. No. 4,183,364, issued Jan. 8, 1980; inventor Gumushan) have been proposed as methods for removing nicotine from tobacco leaves. All of these treatments are designed to maintain the flavour and aroma of the tobacco, and these methods involve extensive post-harvest processing and are therefore not suitable for the preparation of products as described in this invention.

Specific alteration of nicotine levels within tobacco, by either over expression (i.e. increasing) or antisense expression (decreasing) of putrescine N-methyltransferase, a rate limiting enzyme involved in the nicotine biosynthetic pathway, has been suggested (U.S. Pat. No. 5,260,205, issued Nov. 9, 1993 and U.S. Pat. No. 5,369,023, issued Nov. 29, 1994; inventors Nakatani and Malik). These methods are directed to the alteration of nicotine levels so that the levels of other alkaloids that affect the flavours and aroma of tobacco are not modified in any manner. No nicotine free plants were actually produced, nor was the use of these transgenically modified tobacco plants, as a bioreactor for the synthesis of proteins of interest, suggested. However, such methods, if modified to reduce total plant alkaloid levels, may be used in order to produce non-food crop plants wherein total alkaloid levels are reduced.

In order to establish the efficacy of transgene expression in a low-alkaloid plant, a low-nicotine plant, or a low-nicotine low-alkaloid plant, such as, but not limited to 81V-9, several proteins of interest were expressed. These proteins included, but are not limited to IL-4, IL-10, GAD, and a Type II antifreeze protein (AFP). However, any protein of interest may be expressed in a low-nicotine, low-alkaloid tobacco plant.

Administration of cytokines orally may offer an alternative to systemic application or topical application and may have local and systemic effects. Interestingly acid inactivation and protease digestion does not appear to inactivate all cytokine effects, in the limited experience to date using an oral approach. Bioactivity may be retained even in the presence of trypsin and chymotrypsin, at least for IL-6, suggesting heavy glycosylation and other factors confer acids stability to cytokines (Rollwagen and Baqar 1996). Furthermore, interferons can suppress collagen induced arthritis in rats when given in high dose orally. Oral cytokines may simplify an approach to delivery and could be useful in models of infection, HIV, autoimmunity and transplantation rejection. Transgenic plants may also protect a transgenic protein of interest that is administered orally, providing greater resistance to gastrointestinal digestion (e.g. Kong et al., 2001, P.N.A.S. 98:11539-11544). This protection includes the "encapsulation" of transgenic proteins within cytoplasmic micro compartments, as well as the presence of plant glycosylation and other factors which confers as stability to functional proteins such as cytokines and as well the other components of the plant tissue which may further enable the transgenic proteins of interest to reach heights within the GI tract that are responsible for immune modulation, or to reach those sites within the GI tract that are undergoing inflammation such as in inflammatory bowel disease.

Gene constructs were transformed into N. tabacum cv. Xanthi and 81V9-4 tobacco strains (available from Agriculture and Agri-Food Canada, Pest Management Research Center, Delhi Farm, Genetics Section). 81V9-4 is a flue-cured tobacco line containing only trace amounts of alkaloids and is an ideal component for tobacco-based molecular farming applications. Gene constructs were built for production of pro and mature forms of a Type II antifreeze protein (AFP), IL-4, IL-10 or GAD to be accumulated in the cell cytosol and extracellular space. Several different constructs comprising IL-10 were constructed in order to optimize expression of the gene within a non-food crop plant.

Figure 5:
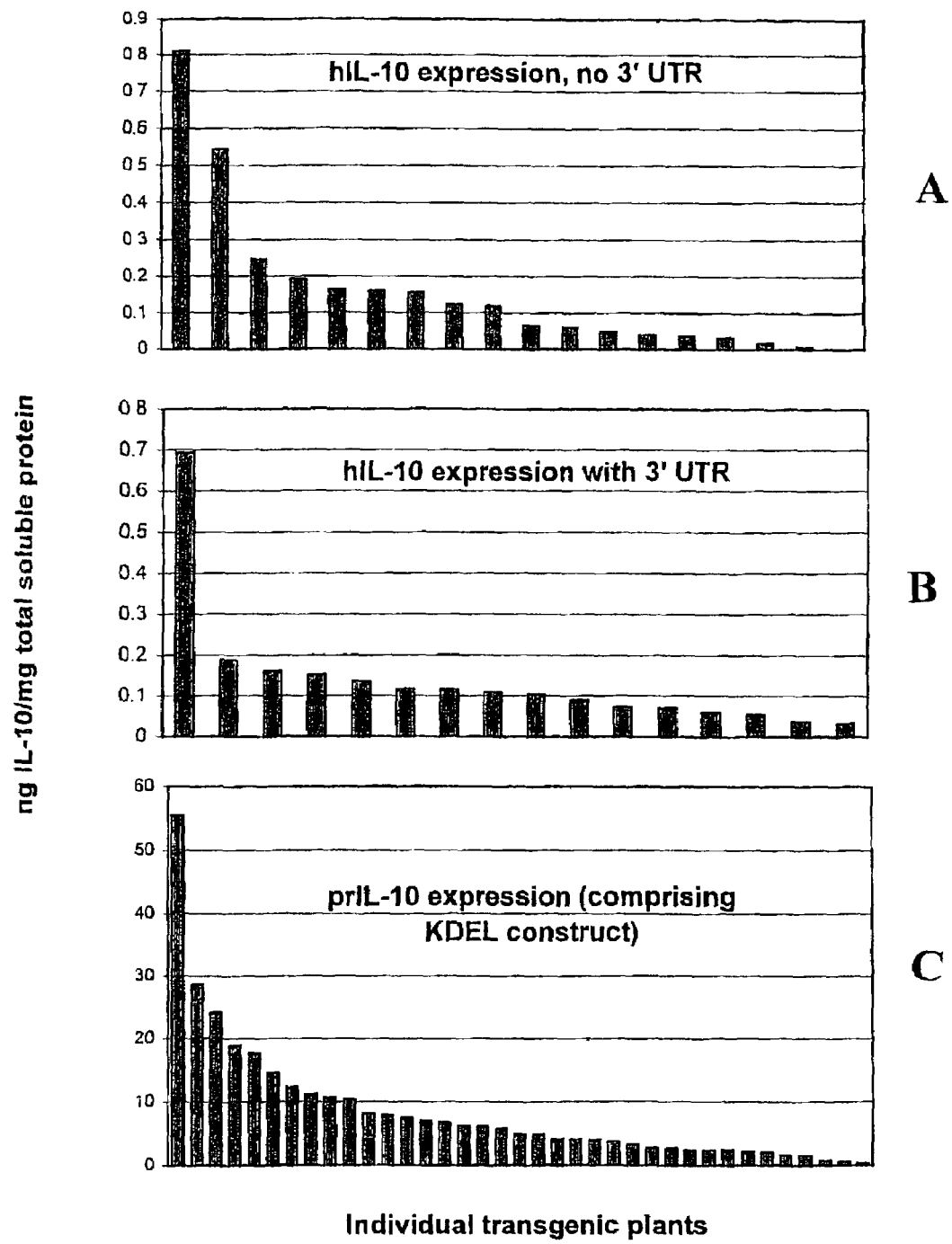
FIG. 5 graphically depicts the expression of human interleukin-10 (hIL-10) in plants.

Using the methods described in Example 3, low-nicotine, low-alkaloid tobacco plants expressing plant recombinant human interleukin-10 (prIL-10) comprising a (thrombin)-(His tag)-(KDEL) sequence were created. Referring now to FIG. 5, there is shown results of the expression of human interleukin-10 (hIL-10) in plants. FIG. 5A and FIG. 5B show the quantity of IL-10 secreted to the apoplast following transformation of tobacco plants with nucleotide sequences comprising either a long hIL-10 3'UTR region or a short hIL-10 UTR region respectively. FIG. 5C shows the quantity of plant recombinant IL-10 expressed in transgenic tobacco plants transformed with an IL-10 nucleotide sequence which further comprises a KDEL endoplasmic reticulum retention signal. The results indicate that human IL-10 may be produced in plants, such as, but not limited to low-nicotine, low-alkaloid tobacco plants.

Figure 6:
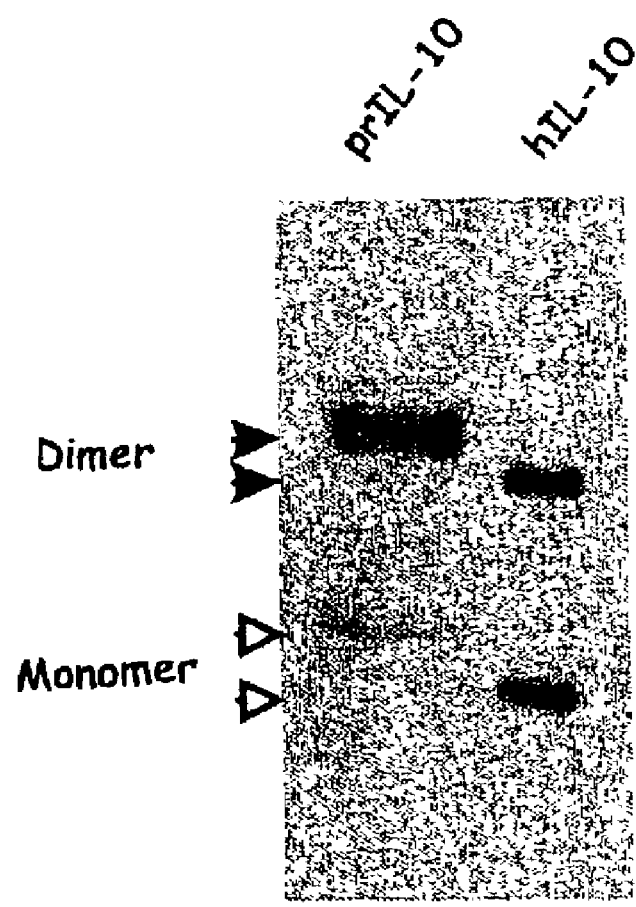
FIG. 6 shows results of the analysis of plant recombinant IL-10 (prIL-10) protein. Non-reducing SDS-PAGE of prIL-10 and hIL-10. Black arrow head means dimer; white arrow head means monomer.

Referring now to FIG. 6, there is shown an immunoblot following non-denaturing SDS-PAGE of recombinant human IL-10 (hIL-10) produced in insect cells and plant recombinant IL-10 (prIL-10). The results indicate that plant recombinant IL-10 is correctly assembled into dimers. The difference between the migration of the prIL-10 and hIl-10 is due to the presence of the (thrombin)-(His tag)-(KDEL) sequence in the prIL-10 protein.

Figure 7:
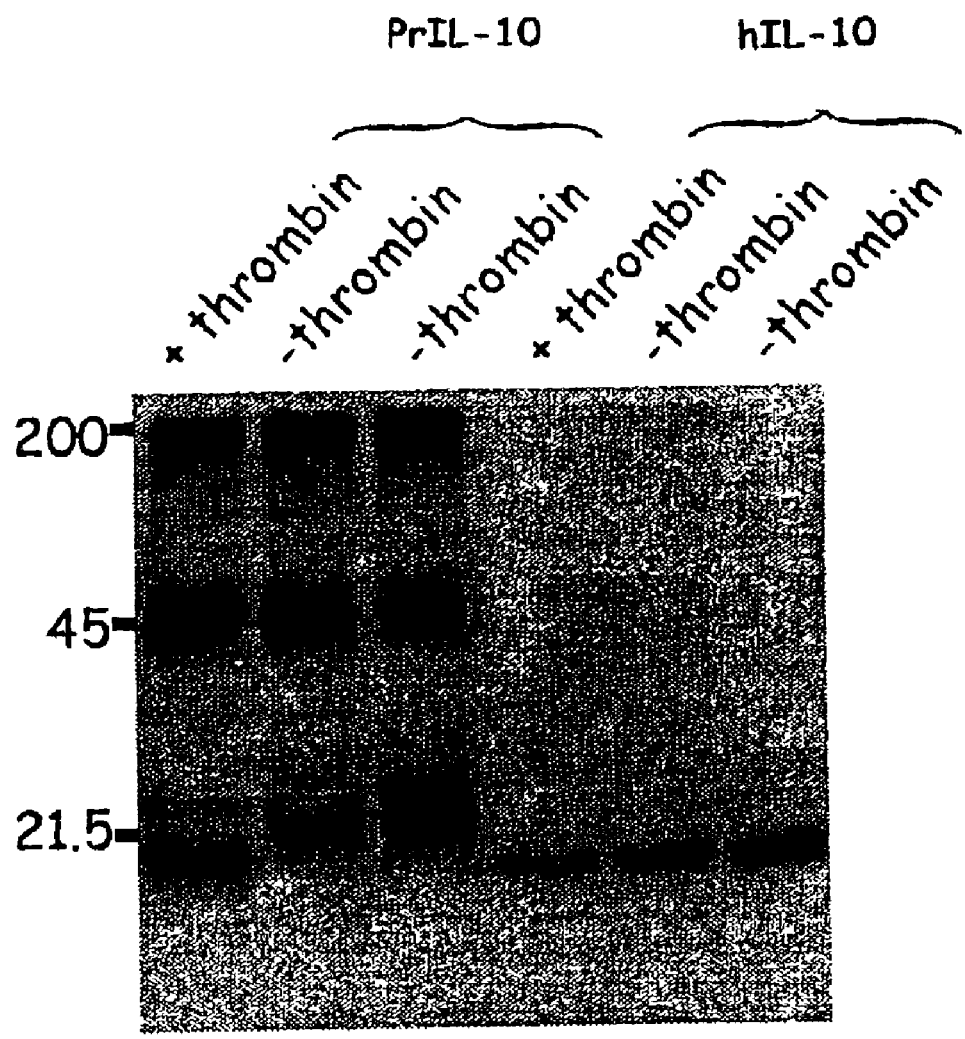
FIG. 7 shows results of reducing SDS-PAGE of prIL-10 and hIL-10, either digested with thrombin (lanes+thrombin), incubated in thrombin buffer (−thrombin a) or untreated (−thrombin b). Molecular weight standards kDa.

Referring now to FIG. 7, there is shown results of digesting plant recombinant IL-10 that comprises the (thrombin)-(His tag)-(KDEL) with thrombin. As shown in FIG. 7, thrombin digestion of the protein indicated that the signal peptide was properly processed in plants.

One important biological role of IL-10 is in sepsis, which is a serious and often fatal consequence of exposure to endotoxins or LPS (Howard et al., (1993) J. Exp. Med. 4, 1205-1208 (Appendix B)). IL-10 inhibits the production of proinflammatory cytokines such as TNF-α and IL-6 by LPS stimulated cells. Complete inhibition requires the intact IL-10 protein, as small synthesized peptides taken from the C and N terminus of the IL-10 protein are ineffective (Gesser, 1997 PNAS 94, 14620-14625). Biological activity was tested by determining its ability to inhibit the LPS induced secretion of IL-6 by the murine monocyte cell line PU51.8. As shown by the results depicted in FIG. 8, plant recombinant IL-10 inhibits LPS induced secretion of IL-6 in a dose dependent manner similar to insect derived human IL-10 (hIL-10). For both proteins, a linear inhibition of IL-6 secretion occurred at concentrations of between about 0.039 and about 2.5 ng per mL. Control protein from an untransformed plant has no effect. These results suggest that plant recombinant IL-10 produced in plants such as low-nicotine, low-alkaloid tobacco plants is biologically active.

Figure 9:
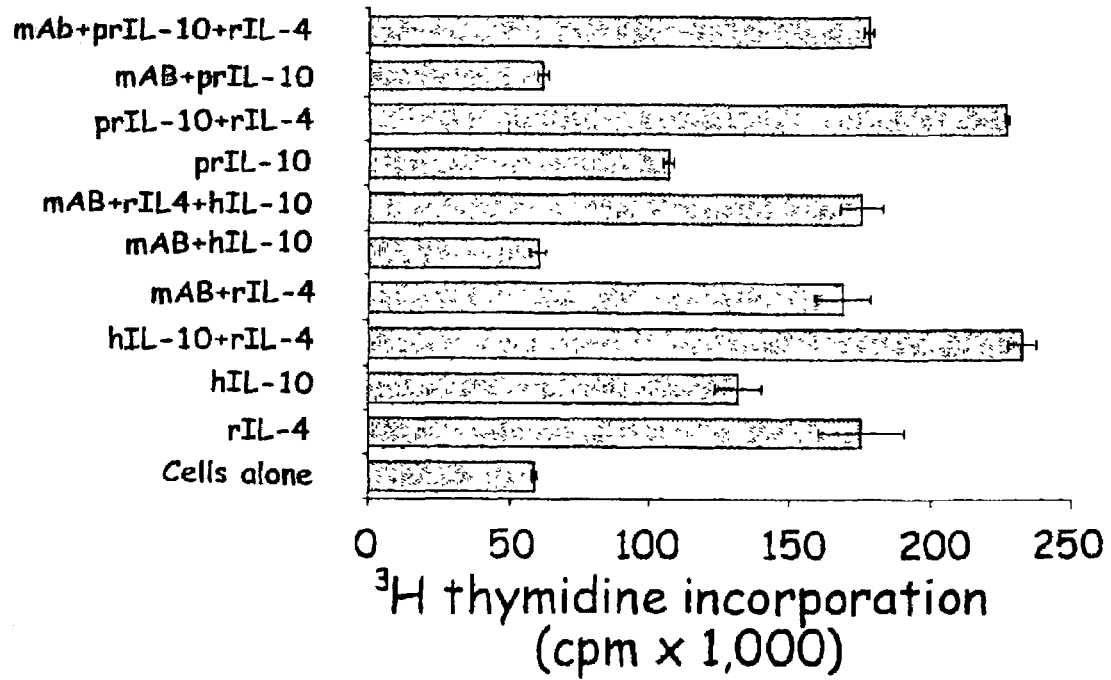
FIG. 9 shows results of the co-stimulatory effect of prIL-10C or hIL-10 on mast cell proliferation. The ability of hIL-10 (2 ng ml$^{-1}$) or prIL-10 (1.27 ng ml$^{-1}$) and rIL-4 (0.08 ng ml$^{-1}$) to enhance growth of MC/9 mast cells was assessed by a [$^3$H] thymidine incorporation assay. Ab: neutralizing anti-IL-10 monoclonal antibody (1 µg ml$^{-1}$); rIL-4: recombinant murine IL-4; prIL-10: plant recombinant human IL-10; hIL-10: recombinant human IL-10 produced in insect.

Human IL-10 is known to induce proliferation of MC/9 murine mast cells. Further, proliferation can be blocked by a monoclonal antibody (mAB) specific for the IL-10 soluble receptor. Referring now to FIG. 9, there is shown results demonstrating that plant recombinant IL-10 induced proliferation of mast cells. Further, the proliferation was blocked by the addition of neutralizing anti-IL-10 mAb, confirming that the proliferation was due to the plant recombinant IL-10 and not other factors present in the purified plant fraction. These results demonstrate that plants are able to express IL-10, and can process and assemble the protein into biologically active dimeric form.

IgG expression in plants lends support to the idea that passage through the endoplasmic reticulum may enhance protein accumulation. In plants bred to simultaneously express mouse IgG light and heavy chain proteins targeted to the extracellular space, the amount of each protein increased up to 60-fold over that seen when expressed individually into the same compartment (Hiatt et al 1989). Expression of both protein components into the cytosol, however, did not affect their level of accumulation. IgG processing and assembly in lymphocytes occurs through the action of heavy-chain binding proteins present in the endoplasmic reticulum (ER). The observed increase in yield when both proteins were targeted to the extracellular space has been attributed to an enhanced stability contingent on IgG assembly. Consistent with this hypothesis, active antibody complexes were observed when the proteins were targeted to the extracellular space but not when targeted to the cytosol.

To further maximize expression levels and transgene protein production the gene encoding the protein of interest, the codon usage within the non-crop plant of interest should be determined. Also, it has been shown that endoplasmic reticulum retention signals can dramatically increase transgene protein levels, for example the KDEL motif (Schouten et al 1996). Replacing any secretory signal sequence with a plant secretory signal will also ensure targeting to the endoplasmic reticulum (Denecke et al 1990).

Thus, according to an aspect of an embodiment of the present invention, there is provided a method for the production of a protein of interest, the method comprising,
 i) selecting a low-nicotine, low alkaloid tobacco plant;
 ii) transforming the plant with a vector containing a gene encoding the protein of interest and operatively linked with 5' and 3' regulatory regions allowing expression of the protein of interest, thereby producing a transformed plant;
 iii) growing and harvesting the transformed plant containing the protein of interest, and;
 iv) obtaining plant tissues from he transformed plant that comprises the protein of interest.

The, present invention also pertain to a method for the production of a protein of interest, the method comprising,
 i) providing a low-nicotine, low alkaloid tobacco plant containing a gene encoding the protein of interest that is operatively linked with 5' and 3' regulatory regions and allowing expression of the protein of interest;
 ii) growing and harvesting the plant containing the protein of interest, and;
 iii) obtaining plant tissues from the plant.

Preferably, the low-nicotine, low-alkaloid tobacco plant exhibits an alkaloid concentration and a nicotine concentration which is less than about 10% the alkaloid concentration and less than about 10% the nicotine concentration of Delgold tobacco plants grown under the same conditions. More preferably, the low-nicotine, low-alkaloid tobacco plant exhibits an alkaloid concentration and a nicotine concentration which is less than about 5% the alkaloid concentration and less than about 5% the nicotine concentration of Delgold tobacco plants grown under the same conditions. Still more preferably, the low-nicotine, low-alkaloid tobacco plant exhibits an alkaloid concentration and a nicotine concentration which is less than about 0.28% the alkaloid concentration and less than about 2.6% the nicotine concentration of Delgold tobacco plants grown under the same conditions.

The protein of interest may be any protein. In an aspect of an embodiment, which is not meant to be limiting in any manner, the protein may be an interleukin, for example, but not limited to IL-4, IL-10, or both. The interleukin may comprise a human interleukin, but is not limited to being human. Further, the interleukin may be genetically modified for example by site-directed mutagenesis or other methods which are known to those skilled in the art.

In another aspect of the present invention which is not meant to be limiting in any manner, the plant may comprise GAD, for example, but not limited to GAD67, GAD65, or a combination thereof. As described previously for plant produced interleukins, the GAD may comprise a human GAD, but is not limited to being human. Further, GAD may be generically modified for example by site-directed mutagenesis or other methods which are known to those skilled in the art.

The protein of interest may also comprise a protease cleavage sequence, for example but not limited to a thrombin cleavage sequence, a localization signal, for example but not limited to an endoplasmic reticulum retention sequence, and an affinity tag sequence to aid in the purification of the protein of interest, for example a HIS tag. Methods of modifying proteins to comprising such sequences are known in the art and within the capability of a person of skill in the art.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

AFP Gene Construction and Expression

To maximize potential AFP production at the translational level, the native 5'-untranslated region of the fish cDNA was replaced with the 5'-untranslated leader region of the tobacco mosaic virus (TMV) (Richards et al 1977 & 1978, Sleat et al 1988). The fish signal peptide sequence was also replaced with that of the tobacco pathogenesis-related protein 1b (PR-1b) (Cornelissen et al 1986, Sijmons et al 1990, Denecke et al 1990). Oligonucleotide cassettes were designed: three oligonucleotides, #1091, (SEQ ID NO:1); #1092 (SEQ ID NO:4); and #1309 (SEQ ID NO:2), which would hybridize to generate the complete TMV leader sequence (TMV Cassette: FIG. 10A); and five oligonucleotides #4361-#4365 (SEQ ID NOs: 3, 5, 6, 8 and 9, respectively) which in concert with oligonucleotides #1091 and #1092 (SEQ ID NO:1 and 4) would hybridize to generate a linked TMV leader and PR-1b signal peptide DNA sequence (TWV-PR Cassette: FIG. 10B). The 5' end of these cassettes corresponded to a BamHI sticky end restriction site. The 3' end of the TMV cassette was blunt and incorporated an additional adenine nucleotide intended to form the first nucleotide of the start codon while the 3' end of the TMV-PR cassette was compatible with NdeI-cut DNA but would not be able to re-generate the restriction site following ligation.

To facilitate addition of the TMV and TMV-PR cassettes, sea raven Type II AFP cDNA was site-specifically mutated according to the method described by Kunkel (1985) to incorporate an NdeI restriction site at either bp 157 or 207. These mutations also introduced appropriate in-frame methionine start codons at the junctions between sequences encoding pre and pro, or pro and mature portions of the AFP. To build the gene construct for accumulation of AFP into the cytosol, plasmids containing the mutated Type II AFP cDNAs were initially cut with NdeI and made blunt-ended with mung bean nuclease. The cDNA fragments were released by cleavage with SalI, were isolated and directionally ligated into a BamHI/SalI-cut pTZ18 vector together with annealed TMV oligonucleotides #1091, #1092 and #1309. The TMV-proAFP and TMV-mAFP constructs were then cut with BamHI and HincII, and the isolated AFP gene fragments ligated separately into pMON 893. For gene constructs targeting AFP to the extracellular space, the mutated Type II AFP cDNAs were initially subcloned from their pTZ 19 vectors into HindIII/SalI-cut pBluescript vectors to position a BamHI restriction site 5' to the AFP coding sequence. The pBluescript-AFP clones were cut with BamHI and NdeI restriction enzymes to remove the sea raven signal peptide sequence or signal peptide and pro-region DNA. The plasmid portions of these digests were isolated and ligated with annealed oligonucleotides #1091, #1092, and #4361 through #4365. The gene constructs were then cut with XbaI and KpnI, and separately cloned into pCDX-1.

Figure 11:
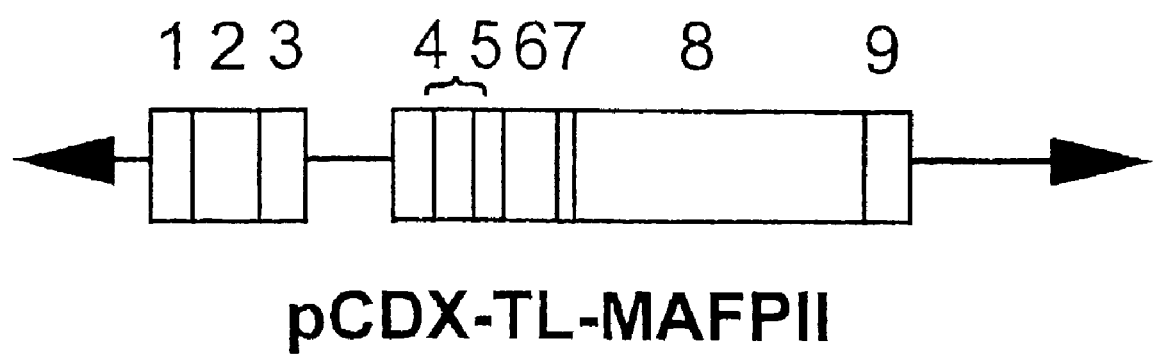
FIG. 11 displays the map of the T-DNA region of pCDX-TL-MAFPII.
Figure 12:
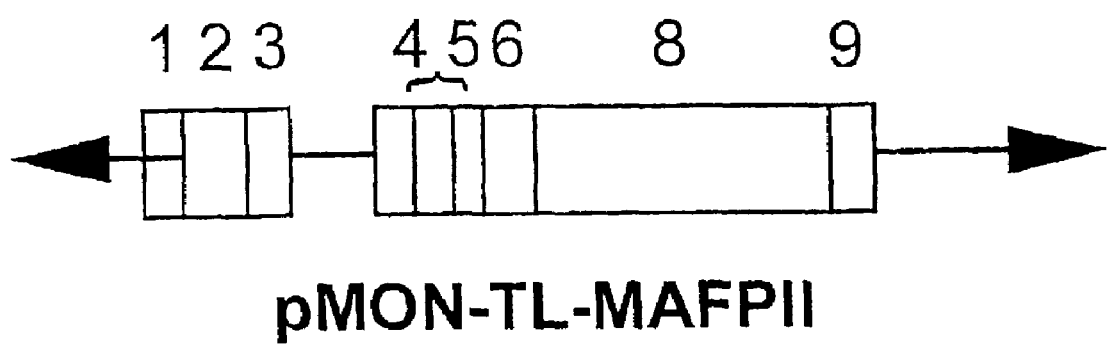
FIG. 12 displays the map of the T-DNA region of pMON-TL-MAFPII.

Cloning of the Type II AFP gene constructs into pMON 893 or pCDX-1 oriented the gene cassette into the vector between the double CaMV 35S promoter (Kay et al 1987) and the NOS polyadenylation sequence. AFP encoded by the transgene constructs was identical to the pro and mature AFP forms present in fish with the exception of one additional methionine at the N-terminal end of the proteins. The T-DNA portion of the final constructs are depicted in FIGS. 11 and 12. Cleavage of the signal peptide components from the expressed AFPs was predicted (von Heijne 1986) to occur immediately prior to the added methionine in both the pro and mature AFP gene constructs so the AFP accumulating in the cytosol and extracellular space should be identical.

Gene constructs were transformed into N. tabacum cv. Xanthi and 81V9-4 tobacco strains according to the method described by Horsch et al (1988). Attempts to generate plants carrying transgenes for cytosolic accumulation of the AFP were made intermittently over a period of several years. Discs infected with A. tumefaciens carrying these gene constructs showed little tendency to form callus and seemed more subject to bacterial infection than comparably treated discs transformed with other transgene constructs. Eventually six transgenic plants were regenerated: one proAFP transgenic in each tobacco strain, three mature AFP transgenics in Xanthi and one mature AFP transgenic in 81V9-4. By contrast, within six months, eight transgenic plants were regenerated carrying gene constructs for AFP accumulation into the extracellular space: two proAFP transgenics in each strain and four mature AFP transgenics in 81V-9. Transformed and regenerated plants were initially selected for kanamycin resistance. Transgenic status was subsequently determined by direct PCR screening for the AFP transgene using primers #3339:

5'-TATTTTTTACAACAATTACCAACAAC-3' (SEQ ID NO:10)

and #4708:

5'-CAGCAGTCATCTGCATACAGCAC-3' (SEQ ID NO:11)

which hybridize to the TMV leader and at the 3' end of the sea raven AFP coding sequence, respectively. Type II AFP gene constructs were amplified in 30 cycles of denaturation for 1 min at 95° C., annealing for 1 min at 55° C., and elongation for 2 min at 72° C. This generated amplification products of 440 and 388 bp from the gene constructs for cytosolic accumulation of the pro and mature AFPs, and 532 and 480 bp fragments from gene constructs designed for accumulation of the same AFPs into the extracellular space.

Analysis of Transgene Expression

Plants were removed from the growth chamber and maintained at room temperature under a grow light for a minimum 48 h prior to RNA or protein extraction. RNA was prepared by selective precipitation according to the method of Palmiter (1974). Total RNA (40 µg) was analysed by Northern blots according to the method of Lehrach et al (1977) and probed with [$\alpha$-$^{32}$P]-labelled sea raven AFP cDNA sequence.

Total soluble protein extracts were prepared from three to four leaves taken from the upper half of a healthy plant according to the method described by Gengenheimer (1990). Extracts were dialysed at 4° C. against 0.1%, 0.01% and 0.001% ascorbic acid in SpectraPor® #3 dialysis tubing (MWCO 3.5 kDa) and centrifuged for 15 min at 12,000×g to remove precipitate formed during dialysis prior to lyophilization. Samples were resuspended in Millipore®-filtered water and their protein concentrations determined by Bradford assay (16) relative to a BSA standard.

To extract protein present in the apoplast by vacuum infiltration (Sijmones et al 1990), leaves were cut longitudinally into 4 cm×0.8 cm strips, and rolled lengthwise in 5 cm×1.8 cm strips of Parafilm® so that the bottom of the leaf was exposed to view. The leaf strip was exposed to vacuum derived from a water aspirator twice for 2 min or until the exposed leaf surface was dark green. Each treated leaf strip yielded 10±2.5 ul of extract. Larger volume samples were too dilute for use and were discarded. Samples which contained green pellets were also discarded to reduce the possibility of cytosolic protein contamination. All remaining extracts from a given plant were pooled and the amount of protein present determined by Bradford (1976) protein assay relative to a BSA standard. Extract concentrations were generally between 0.1-0.2 µg/µl.

Western Analysis

Lyophilized protein was resuspended directly in loading buffer (60 mM Tris-HCl, pH 6.8/10% glycerol/5% β-mercaptoethanol/2% (w/v) SDS/$1.3 \times 10^{-3}$% (w/v) bromophenol blue), and were electrophoresed through a 17% polyacrylamide/0.1 M sodium phosphates, pH 6.8/4 M Urea/0.1% SDS gel using 0.1 M sodium phosphate, pH 6.8/0.1% SDS running buffer. Electrophoresis was conducted at 50 V for 3-4 h or until the 6 kDa pre-stained marker was at the bottom of the gel. Western blots were prepared according to the method described by Burnette et al (1981) and probed with polyclonal antibody to the mature sea raven AFP. A chemiluminescence detection kit (Amersham) for probing of Western blots was used to detect bound first antibody. All reactions were carried out according to the manufacturer's directions.

AFP Gene Expression and Protein Accumulation

Figure 13:
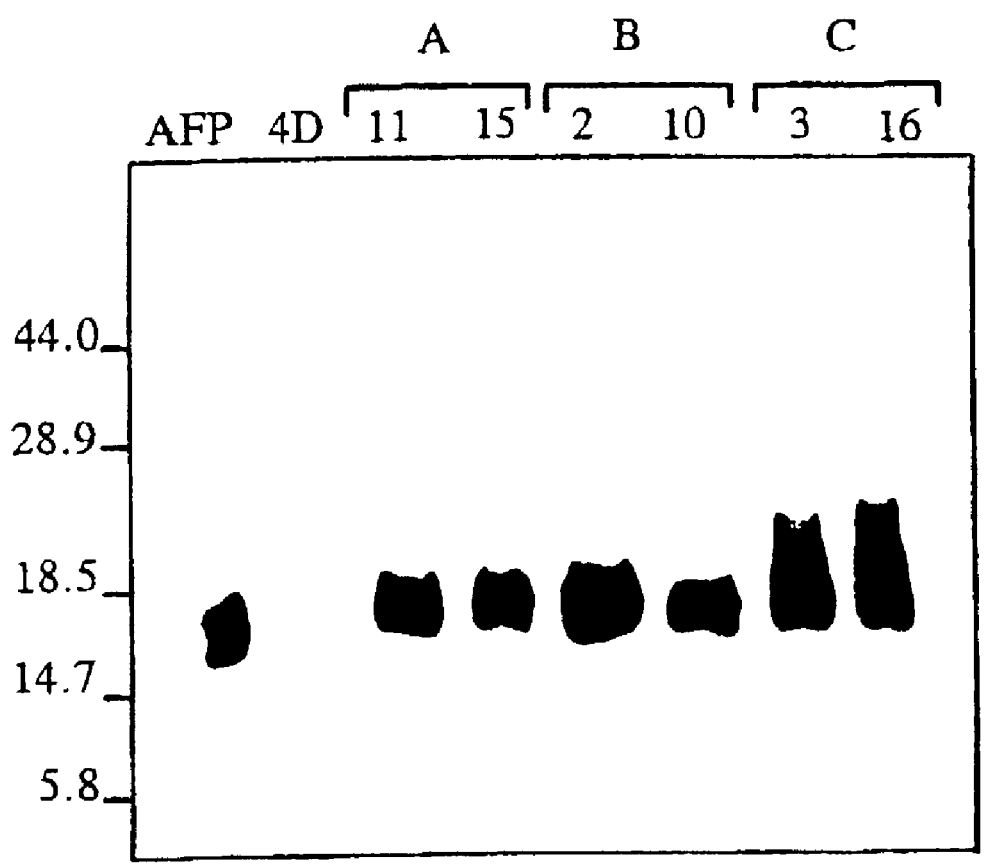
FIG. 13 is a Western blot showing Type II AFP accumulation in field plants. Western blot analysis of total soluble protein (2.5 µg) extracts from R1 generation Type II AFP transgenic plants in which the AFP was targeted to accumulate in the extracellular space. Samples are designated by number to indicate the plot from which it was collected and by letter to indicate the transformed parent plant from which the R1 plants were descended. Records at the Delhi station indicate that A plants were descended from parent II4c$^2$-#10, B plants from II4c$^2$-#1, C from pII3a-#7, and D plants were wild-type controls (4D). Total soluble protein extract from a field-grown wild type plant was included in the analysis as a negative control and mixed with mature Type II AFP (25 ng) purified from sea raven sera to generate the positive control (AFP).

Western blot analysis of total soluble protein extracted from plants carrying genes for cytosolic AFP expression did not find evidence of either pro or mature AFP accumulation even when up to 80 µg of protein extract were analysed. In contrast, a protein which co-migrated with mature AFP from sea raven and cross-reacted with antibody to Type II AFP was detected in as little as 2.5 µg total soluble protein extract of plants in which the AFP was targeted to the extracellular space (FIG. 13). This protein was unique to the transgenic plants and was absent in extracts of a wild-type plant and a plant, pII3a-#9, which had been transformed and regenerated but determined to be non-transgenic by PCR. Insufficient resolution was obtained with these extracts to differentiate size differences between the AFPs produced by the plants carrying transgenes for production of pro or mature AFPs. This was probably due to the viscosity of the total soluble protein extracts which often caused distortion of samples during the running of gels. For this reason, positive control Type II AFP was mixed with total soluble protein extract from a lab-grown wild-type plant to generate a suitable size standard. Wild-type protein extract was not mixed with the molecular weight markers, so the size of plant-produced AFP could not accurately be estimated from these extracts. AFP accumulation varied between plants and appeared slightly higher in plants II4c$^2$-#1 and 10 which carried genes for mature AFP production. Based on Western blot comparison with a known amount of Type II AFP, the amount of AFP produced by the plants has been estimated to be approximately 0.5-1% of the total soluble protein.

mRNA Transcription from Transgenes for Cytosolic AFP Accumulation

RNA extracts of plants transgenic with gene constructs for cytosolic AFP accumulation were analysed by Northern blot to determine if the AFP transgene was transcribed. Two plants, Xanthi TmSR #1 and 81 V9-4 TmSR #1, carrying transgenes for AFP accumulation into the cell cytosol were found to produce a 0.96 kb RNA transcript which hybridized with the AFP cDNA used as a probe: on longer exposure of the blots, the same RNA transcript was also seen in extract from Xanthi TmSR #2 and slightly larger one of approximately 1.02 kb was detected in extract from 81 V9-4 TpSR #3. Transcripts from pro and mature AFP transgene constructs were expected to differ by 51 nucleotides. Both plant-produced AFP gene transcripts were both considerably larger than a PCR-generated control sample estimated to be 0.36 kb and representing the size of the mature AFP transgene between the TMV leader and the 3' end of the coding sequence. This was consistent with the size difference expected based on the additional coding sequence and 3-untranslated region (155 nt total) present in the transgene construct, and with the use of the NOS polyadenylation sequence to obtain polyadenylated transcripts. Both transcripts were smaller than an equivalent gene transcript of 1.06 kb produced in a plant carrying the transgene for targeted mature AFP accumulation into the extracellular space. This size difference was consistent with the addition of the 90 nt signal peptide coding sequence to the transgene construct for secretion of the AFP. Based on EtBr staining, more RNA was loaded onto the gel from the plant producing AFP for accumulation into the extracellular space compared to the amount of RNA from the plants targeting the AFP to the cytosol. No comparison could be made regarding the relative amounts of AFP mRNA transcribed from these constructs. However, similar loadings were achieved between the plants targeting the AFP to the cytosol. The difference in amount of transcript observed, therefore, suggests that this transgene construct was being expressed at variable levels in the different plants.

AFP Present in the Apoplast

Vacuum infiltration extracts were prepared from AFP-producing plants to determine if the expressed AFP was present in the extracellular space. These extracts were not subject to the viscosity and sample distortion associated with total soluble protein extracts, so were also considered more suitable to estimate the sizes of the plant AFPs. Western blot analysis confirmed the presence of AFP. AFP was detected in plants pII3a-#7 and II4c$^2$-#1 which carried mature and proAFP transgenes respectively, as a diffuse band of approximately 14.7 kDa which migrated at a similar rate to mature AFP isolated from fish sera. A small mobility difference was observed between the AFPs produced by the two plants, however, proAFP isolated from fish sera was distinctly larger than either plant-produced AFP.

Having, established the presence of AFP in vacuum infiltration extracts of those plants carrying transgenes for extracellular AFP accumulation, the extracts were concentrated ten-fold and tested for thermal hysteresis activity and effects on ice crystal morphology using the nanolitre osmometer. Extracts from plants expressing gene constructs for either the pro or mature AFP both showed evidence of AFP activity. Ice crystals grown in these plant extracts were seen as the characteristic eye-shaped bipyramids produced in the presence of native Type II AFP. Thermal hysteresis activity was measured and based on comparison with a standard activity curve the amount of active AFP present in the extracellular space was estimated as 2% of the total protein present in the compartment.

RNA analysis of the transgenic plants has shown that they are able to transcribe the integrated transgene constructs, and that the size of the plant AFP mRNA from both construct types is consistent with that expected for a full-length, polyadenylated transcript. mRNA produced from the transgene for AFP accumulation into the extracellular space was obviously translatable.

The presence of plant-produced AFPs in vacuum infiltration extracts indicates that the plant recognized the PR-1b signal peptide component and correctly targeted the attached AFPs to the extracellular space. The predicted size of the AFPs for export to the extracellular space is 18.7 or 17 kDa with the signal peptide component attached and 15.8 or 14.1 kDa without the signal peptide for the pro and mature AFPs, respectively. Western blot analysis of the plant vacuum infiltration extracts showed that the AFPs produced from the proAFP and mature AFP transgene constructs and present in the extracellular space both co-migrated with mature Type II AFP and were approximately 14.7 kDa. This suggests that not only is the plant capable of cleaving the signal peptide from the expressed AFP but that it can remove most or all of the pro-region of the AFP.

Example 2

IL-4 Expression and Determination of Biological Activity

Mouse IL-4 is a glycoprotein of 140 amino acid residues including a putative 20-amino acid signal peptide, which has a molecular weight of 19 to 21 kDa, depending on the degree of glycosylation (Proc. Natl. Acad. Sci. USA 83:2061, 86). Mouse IL-4 cDNA was first amplified with PCR using the primers:

5'-AAT CTCGAGCATATC CAC GGATGCGAC-3' (SEQ ID NO: 13) and

5'-ATAGGTACCGTAATCCATTTGC ATGATGC-3' (SEQ ID NO:14), and the PCR product encoding the full protein was isolated and ligated to a signal peptide encoding sequence from peanut peroxidase and the KDEL sequence (SEQ ID NO:21). To facilitate subsequent purification of the recombinant product from plant cells, a DNA sequence encoding 6 consecutive histidines was also included in the reconstituted IL-4 gene. The reconstituted IL-4 cDNA was then used to replace the b-glucuronidase (GUS) gene in plasmid pTRL2-GUS composed of a CaMV35S promoter with a double enhancer sequence (Ehn-35S) linked to a 5' untranslated tobacco etch virus leader sequence, GUS and a nonpaline syntase (NOS) terminator. The resulting IL-4 expression cassette was inserted into the binary plant expression vector pBin19, and then transferred into the *Agrobacterium tumefaciens* strain LBA4404 (pAL4404) for plant transformation.

Transformation of *Nicotiana tabacum* cv. SR1 was by leaf disc cocultivation with *A. tumefaciens* LBA4404 harbouring IL-4 using procedures described previously (Ma et al, 1997). Mature plants were generated from regenerated shoots under antibiotic selection in hormone-free rooting medium, and then subjected to screening for recombinant protein expression. Transgenic plants expressing the highest levels of transgene proteins were selected for long-term maintenance.

Western Blot Analysis and Chemiluminescent ELISA.

Tobacco plants (*Nicotiana tabacum* cv. SR1) were transformed with the plant expression vectors comprising a mouse IL-4 gene by *A. tumefaciens*-mediated leaf explant transformation method. The regenerated tobacco plants were then analyzed for the presence of mIL-4 DNA, its specific mRNA transcripts and protein products. The leaf tissue from IL-4 transgenic tobacco was homogenized on ice in extraction-buffer (25 mM Tris-HCl, pH 8.0, 50 mM NaCl, 0.1% SDS, 2 mM 2-mercaptoethanol, 1 mM PMSF, 2 mg/ml Leupeptin, 2 mg/ml Aprotitin, and 2 mg/ml Pepstatin A). The tissue homogenates were centrifuged at 4 C. for 15 min at 14,000 g and the concentration of proteins in the supernatants was determined by protein assay (Bio-Rad, Canada). Samples of proteins were separated by SDS polyacrylamide gel electrophoresis, proteins were transferred onto PDF membrane by electroblotting and the recombinant protein was detected by incubation with anti-mouse IL-4 antibody (PharMingen) and a horseradish peroxidase-conjugated secondary antibody and ECL detection reagents (Amersham). Immunoblot analysis of protein homogenates from IL-4 transformed tobacco leaf tissues sowed a unique protein band recognized by monoclonal antibody specific for mouse IL-4 (FIG. 2, lane 3), which is comparable in length to standard recombinant mouse IL-4 (FIG. 2, lane 1).

The level of IL-4 production in transgenic tobacco leaf tissues was determined by chemiluminescent ELISA. Briefly, for quantification of plant-derived recombinant mouse IL-4 (prIL-4), the 96-well microtiter plates (Nunc, Roskilde) were coated overnight at 4° C. with 2 mg/ml anti-IL-4 capture mAb (clone 111311; PharMingen) in 100 ml binding buffer (0.1 M Na2HPO4, pH 9.0). The plates were then washed three limes with PBS containing 0.5% Tween 20, blocked with 1% BSA in PBS, washed and incubated with leaf extracts and mouse rIL-4 standard (Pharmingen), overnight at 4° C. The plates were washed again and incubated with biotinylated mouse anti-IL-4 detection mAb (clone BVD6-24G2, PharMingen, 1 mg/ml) for 1 h at room temperature, followed by avidin-horseradish peroxidase (HRP) and ABTS substrate (both from Sigma Chemical Co., Oakville, Ontario) for 30 min at room temperature for colour development. ODs were read by a Microplate reader (ML3000, Dynatech Laboratories) at 405 nm to determine the relative amounts of recombinant IL-4 in the extracts. The expression level of plant-derived recombinant mIL-4, as determined by IL-4-specific ELISA, was found to be approximately 0.02% of total leaf proteins.

Determination of Biological Activity of Plant-derived Recombinant IL-4.

Although recombinant IL-4 could be detected by both western blot and ELISA, it was important to demonstrate its biological activity. IL-4 was fist described as a T-cell-derived B-cell growth factor (Howard et al., 1982), and has now been shown to mediate a wide array of biological effects on the immune system including growth stimulation for B cells, T cells and mast cells (Hu-Li et al., 1987; Lee et al., 1986). Measurement of IL-4 dependent cell proliferation is considered to be a sensitive bioassay for IL-4 activity. The in vitro T-cell proliferation and cytokine induction were determined as previously described. Briefly, a spleen cell suspension was prepared from individual mice in ice-cold PBS. The spleen cell suspension was cultured in 96-well flat-bottomed plates at $2\times10^5$ cells/well in RPMI (Bio Whittaker, Walkersville, Md.) supplemented with 10% FCS (Life Technologies, Grand Island, N.Y.).

Cultures were stimulated with purified hGAD (10-20 mg/ml) or OVA (10 mg/ml, Sigma) as a negative control. Cells were harvested after 72 h, and were then assayed for the incorporation of [3H]thymidine (1 mCi/well; Amersham, Oakville, Ontario, Canada) added during the last 18 h of culture. Accordingly, plant-derived recombinant IL-4 was tested with the MC/9 murine mast cell line (obtained from the American Type Culture Collection, Rockville, Md.) which requires IL-4 for proliferation. As shown in FIG. 3, proliferation of mast cells occurred with both plant-derived recombinant IL-4 (prIL-4) and control standard rIL-4 (Pharmingen), suggesting that plant-derived recombinant IL-4 is biologically active, a function that is desirable for use as an immunomodulator in oral tolerance.

Oral Administration of Low-dose IL-4 Does Not Significantly Alter Serum IL-4 Levels The in-vivo activity of plant produced IL-4 is determined in NOD mice. NOD and control strain (insulitis- and diabetes-free) female mice (20 mice/group) are fed either transgenic low nicotine tobacco leaves expressing recombinantly produced IL-4. At various times during the 4 week treatment, circulating serum levels of plant recombinant IL-4-fed and un-fed NOD and control mice are analyzed by ELISA as described above. Both NOD and control mice are monitored for any potential toxic effects arising from the plant recombinant IL-4 feeding, and their serum concentrations of IgE and IgG quantified by ELISA. Briefly, serum samples were added at appropriate dilutions to microtiter plates coated with 2 mg/ml of purified anti-mouse IgE capature mAb (clone R35-72; PharMingen). Biotinylated anti-mouse IgE mAb (2 mg/ml, clone R35-118; PharMingen) together with avidin-peroxidase and ABTS substrate were used for detection. No serum IgE concentrations were found to be significantly elevated in IL-4 treated mice compared to that in control-treated mice under the conditions tested. Thus, administration of low dose IL-4 does not induce an appreciable increase in serum IgE concentration.

Feeding of plant recombinant IL4 to protect against the onset of insulitis and/or Type 1 diabetes in NOD mice is also determined. Pre-diabetic female NOD mice (4 weeks of age) fed or not fed with plant recombinant IL-4 are maintained in a specific pathogen free animal facility. Mice are monitored weekly for their blood glucose levels (BGL), and mice that are hyperglycemic (i.e. BGL>11.1 mmol/L) for two consecutive weeks are diagnosed as Type 1 diabetic. The onset of insulitis is monitored by immunohistochemical analysis of pancreatic tissue by sacrificing mice at various times (2 weeks to 2 months) after plant recombinant IL-4-feeding is initiated.

Example 3

Interleukin-10 (IL-10) Expression and Determination of Biological Activity

Full length mRNA encoding human IL-10 (hIL-10) is 1601 nucleotides long, with a short 5' UTR of 30 nucleotides (nt) and a long 3' UTR of 1037 nt. The hIL-10 coding sequence is 534 base pairs long and codes for a 178 amino acid preprotein with a 18 amino acid secretory signal (Vieira et al., 1991). The full length human IL10 cDNA is isolated from polyA RNA by RT-PCR and fully sequenced to ensure fidelity. In order to maximize expression levels and transgene protein production, the IL10 cDNA is examined for codon usage patterns and optimized as necessary (Perlak et al. 1991).

Since ER retention signals can increase the concentration of disulfide bonded transgene proteins, therefore the KDEL ER retention motif may be added to the IL-10 cDNA using site directed mutagenesis (see results in FIG. 5(C)). For comparative purposes an identical synthetic gene, without the KDEL signal, is prepared and used in the transformation studies (SEQ ID NO:12).

The expression system adopts a duplicated 35S enhancer-promoter plus AMV leader sequence (Kay et al. 1987; Jobling and Gehrke 1987). However other constitutive promoters may also be employed, for example, T1276 a constitutive promoter from tobacco (see co-pending application U.S. application Ser. No. 08/593,121). The IL-10 gene is cloned into a T-DNA vector between the T-DNA border sequences using the Bin19 derived plant expression vector pCamTerX. The synthetic IL-10 gene is transformed to tobacco using *Agrobacterium* mediated transformation (Horsch et al. 1989). The *Agrobacterium* strain used is EHA101 carrying the disarmed Ti plasmid pEHA104. The plant selectable marker is neomycin phosphotransferase.

To maximize transgene expression and ensure stable field performance a large number of primary transformants need to be generated, selected for expression levels, screened for copy number, and single-copy high-expressing lines evaluated for field performance. Standard methods (e.g. Northern and Western blotting) are used to evaluate expression levels (Sambrook et al. 1989). ELISA is used to quantify transgene protein yields.

Figure 15:
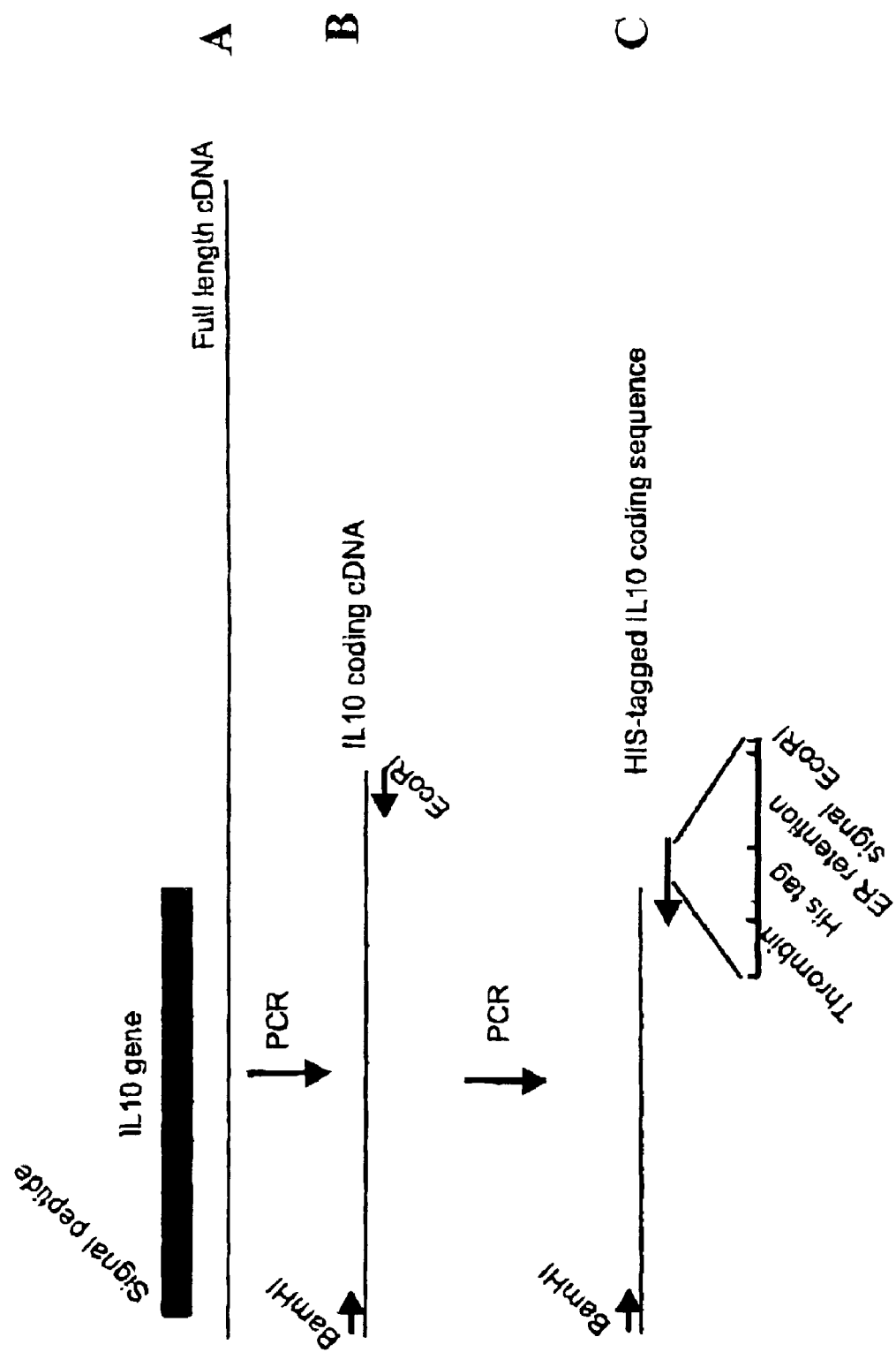
FIG. 15 shows a schematic depiction of three IL-10 constructs used in plant transformation as described herein.
Figure 16:
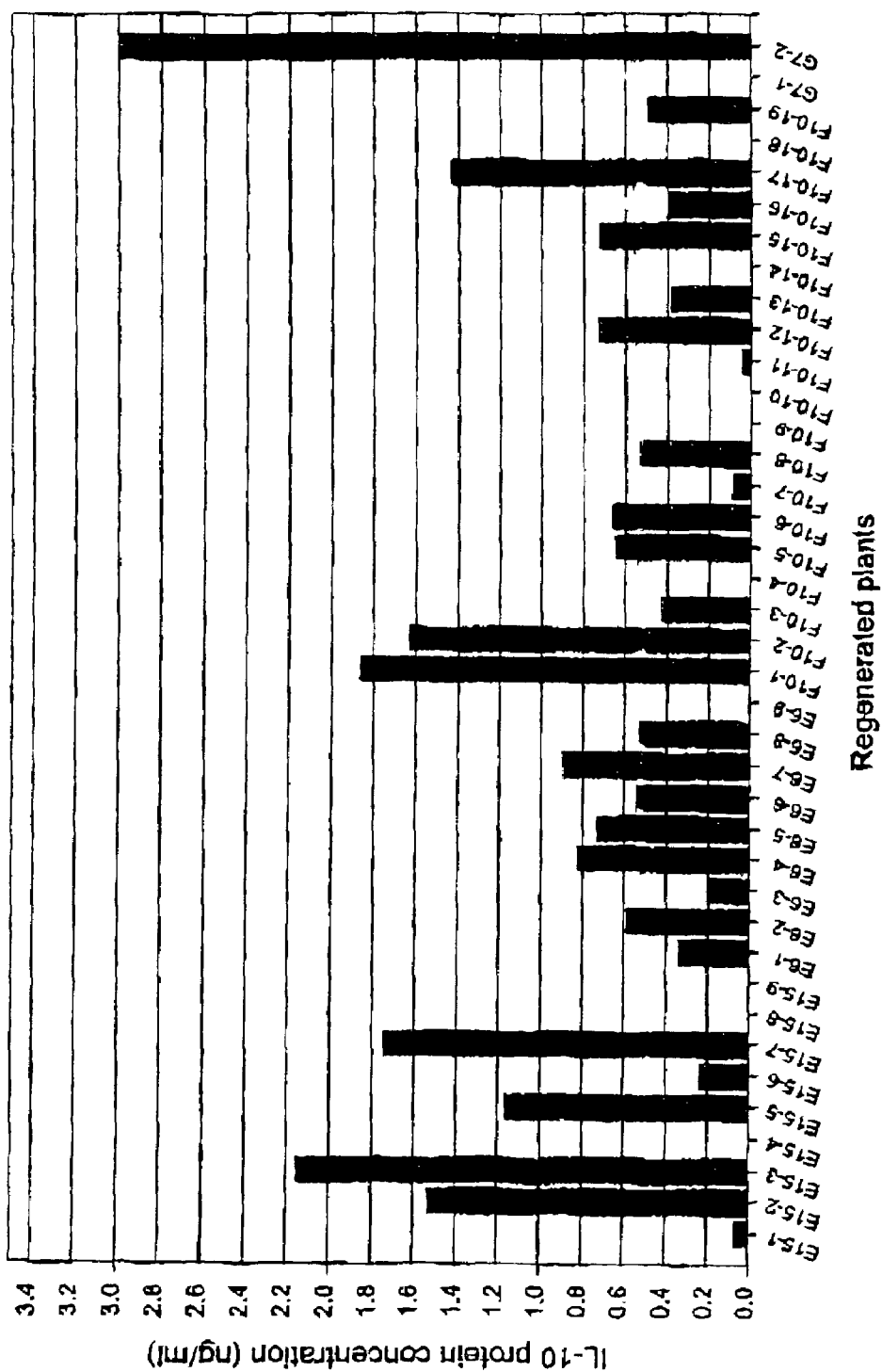
FIG. 16 shows the IL-10 protein levels within transgenic plants as determined by ELISA. The protein concentration was determined and compared against a hIL-10 standard curve. Individual transformed plants were analyzed. Plants denoted "E" were transformed with hIL-10 construct containing coding sequences and a short 3' UTR; plants denoted "F" were transformed with hIL-10 construct containing coding sequences and the complete 3' UTR; plants denoted "G" were transformed with hIL-10 construct containing coding sequences fused to thrombin-His tag-KDEL sequence.

A sequence containing the hIL-10 open reading frame and a truncated 3' UTR (nt 4-732) is amplified by PCR using oligonucleotides hIL-10-5'-BamHI and hIL-10-3'-EcoRI (FIG. 15(B); transformed plants comprising this contruct are denoted "E" in FIG. 16, and see FIG. 5(A). The 5' oligonucleotide is designed with a BamHI site at the 5' end, and the 3' oligo is designed with an EcoRI site at the 5' end. These restriction sites enable the easy directional cloning of the construct in the phagemid pBluescript (Stratagene) and in the Bin 19-derived binary vector pCaMter X (Frisch et al., 1995). To determine the effect of the 3' UTR on expression of hIL-10 in plants, the complete cDNA (4-1601; FIG. 15(A); transformed plants comprising this contruct are denoted "F" in FIG. 16, and FIG. 5(B) is also cloned into pBluescript and pCaMter X.

To maximize protein accumulation in the plant cell, the endoplasmic reticulum (ER) retention signal, KDEL (Schouten et al., 1996), is added to the 3' end of hIL-10 coding sequence (FIG. 14); transformed plants comprising this construct are denoted "G" in FIG. 16, and FIG. 5(C). A His tag is also added before the KDEL signal to facilitate purification of the transgenic protein (see FIG. 15(C), and SEQ ID NO:12, nucleotides 544-630). A thrombin recognition sequence is inserted immediately preceding the His tag that allows the cleavage of the His Tag and the KDEL peptides. This third construct encodes a preprotein of 197 amino acids. A single oligonucleotide is used to fuse these sequences to the end of hIL-10 reading frame (see FIGS. 14 and 15). This oligonucleotide is used in conjunction with oligonucleotide hIL-10-5'-BamHI in a PCR to generate the fragment which was then cloned both in pBluescript and in pCaMter X.

Cloning of the IL-10 gene constructs into pCaMter X orientes the gene between the double CaMV double 35S promoter (Kay et al., 1987) and the NOS (Nopaline synthase) polyadenylation sequence (Frisch et al., 1995). The plant recombinant IL-10 (prIL-10) encoded by the native transgene constructs was identical to the native human IL-10. After purification and thrombin cleavage, the prIL-10 encoded by the tagged construct differs in only its two terminal amino acids from the native hIL-10.

Gene constructs are transformed into *N. tabacum* cv. 81V9-4 low alkaloid tobacco strains according to the method described by Miki et al. (1998). Transformed and regenerated plants are initially selected for kanamycin resistance. Regenerated plants are analyzed for expression of the IL10 protein by solid phase sandwich Enzyme-Linked ImmunoSorbent Assay (ELISA). Briefly, the JES3-9D7 anti-IL-10 mAB (PharMingen) is used as a capture antibody and is paired with the biotinylated JES3-12G8 anti-IL-10 mAB (PharMingen) as the detecting antibody. Recombinant human IL-10 (PharMingen) is used as standard.

Leaf tissue (1 g of fresh weight) was ground in 2 ml of extraction buffer (phosphate buffered saline (PBS) pH 7.4, 0.05% (v/v) Tween 20, 2% (w/v) polyvinylpolypyrrolidone (PVPP), 1 mM phenylmethylsulfonylfluoride (PMSF), 1 µg/ml Leupeptin) and clarified by centrifugation at 13,000 g for 15 min at 4*C. The supernatant containing total soluble proteins was analyzed directly in a hIL-10 ELISA using standard protein and antibodies as per the supplier's protocol (Pharmingen). The results are presented in FIG. 16.

Leaf Tissue from transgenic plants containing HIS-tagged phIL-10C (plant human IL-10C) was ground (1 g fresh weight in 3.5 ml buffer) in 20 mM Tris pH 8, 100 mM NaCl, 0.1% (v/v) Tween 20. The extract was clarified by centrifugation, and the supernatant was filtered through a 0.22 µm membrane. prIL-10C was purified by IMAC on a chelating Hi-Trap column (Amersham Pharmacia). The presence of phIL-10C in the eluted fractions was assessed by immunoblotting using biotinylated polyclonal anti-IL-10 antibodies (1:1000 R&D systems), Streptavidin-HRP (1:3000 Genzyme) and ECL detection reagents (Amersham Pharmacia). Protein was quantitated using the Bradford method. Thrombin (1 unit, Novagen) was used to digest 1 ng of insect recombinant IL-10 or phIL-10C in a 20 µl reaction in 20 mM Tris-HCl pH 8.4, 0.15 M NaCl, 2.5 mM $CaCl_2$ for 16 hours at 23° C.

Eighteen transgenic plants are regenerated from the native construct containing only a short stretch of 3' UTR (called E6 and E15 in FIG. 16), and nineteen plants are regenerated from the native construct containing the entire 3' UTR (called F10 in FIG. 16). All of those and the first two plants regenerated from the construct containing the His tag and KDEL ER retention signal (called G7 in FIG. 16) are tested for presence of IL-10 protein by ELISA.

A variable level of plant recombinant IL-10 (prIL-10) is observed in the regenerated plants. There were no marked differences between plants transformed with the full-length hIL-10 cDNA and those transformed with 3' truncated cDNA. However, the highest level of prIL-10 is obtained in one of the two plants transformed with the construct containing the ER retention signal, G7-2.

The results in FIG. 5(A) and FIG. 5(B) show the quantity of IL-10 secreted to the apoplast following transformation of tobacco plants with nucleotide sequences comprising either a long hIL-10 3'UTR region or a short hIL-10 UTR region respectively. FIG. 5(C) shows the quantity of plant recombinant IL-10 expressed in transgenic tobacco plants transformed with an IL-10 nucleotide sequence which further comprises a KDEL endoplasmic reticulum retention signal. The results demonstrate that human IL-10 may be produced in plants.

Western analysis of extracts of recombinant human IL-10 (hIL-10) produced in insect cells and plant recombinant IL-10 (prIL-10) are shown in FIG. 6. The results indicate that plant recombinant IL-10 is correctly assembled into dimers. The difference between the migration of the prIL-10 and hIl-10 is due to the presence of the (thrombin)-(His tag)-(KDEL) sequence in the prIL-10 protein.

Western analysis of digested plant recombinant IL-10 that comprises thrombin cleavage sire-His tag-KDEL (hIL-10) with thrombin is shown in FIG. 7 and indicates that the signal peptide was properly processed in plants. No digestion was observed in the insect produced IL-10 lacking the thrombin cleavage site.

Functional activity of prIL-10 was assessed in two independent assays. First, the ability of prIL-10 to inhibit the secretion of IL-6 by lipopolysaccharide (LPS)-stimulated (20 µg $ml^{-1}$) macrophages was evaluated. ELISA was used to measure IL-6 (Pharmingen) levels in the culture supernatant of the murine monocyte/macrophage cell line PU5-1.8 (ATCC) stimulated by varying doses of rIL-10 (Pharmingen), prIL-10 purified by IMAC, or control plant proteins (Florentino et al. 1991. J. Immunol. 147:3815-3822 1991). Second, the ability of IL-10 to enhance the IL-4 dependent proliferation of the mast cell line MC/9 (ATCC) was measured. MC/9 cells were grown for 2 days in varying doses of rIL-10 and phIL-10C in the presence or absence of rIL-4 and in the presence or absence of 1 µg of neutralizing anti-human IL-10 mAB (Pharmingen) (Zheng et al. 1995. J. Immunol. 154:5590-5600). Cells were pulsed for 16 h with 1 µCi $well^{-1}$ [$^3$H] thymidine and cultures were harvested in glass fiber filters and counted in a liquid scintillation counter. Proliferation was assessed by measuring the incorporation of [$^3$H] thymidine. In both bioassays, the commercial rIL-10 was calibrated to an IL-10 reference reagent (5000 reference units (RU) per microgram) obtained from the National Cancer Institute.

IL-10 inhibits the production of proinflammatory cytokines such as TNF-α and IL-6 by LPS stimulated cells, however, complete inhibition requires the intact IL-10 protein. Biological activity of recombinant IL-10 was tested by determining its ability to inhibit the LPS induced secretion of IL-6 by the murine monocyte cell line PU51.8. Plant recombinant IL-10 (prIL-10) inhibits LPS induced secretion of IL-6 in a dose dependent manner similar to insect derived human IL-10 (hIL-10) as shown in FIG. 8. For both proteins (insect and plant produced IL-10), a linear inhibition of IL-6 secretion occurred at concentrations of between about 0.039 and about 2.5 ng per mL. Control protein from an untransformed plant has no effect. These results demonstrate that prIL-10 produced in plants is biologically active.

Human IL-10 is known to induce proliferation of MC/9 murine mast cells. As shown in FIG. 9, addition of plant recombinant IL-10 (hIL-10), or rIL-4 and hIL-10 induced proliferation of mast cells.

Cell proliferation can be blocked by a monoclonal antibody (mAb) specific for the IL-10 soluble receptor. As shown in FIG. 9, cell proliferation was blocked by the addition of neutralizing anti-IL-10 mAb (Pharmingen), in the presence or absence of rIL-4, (see Example 2) confirming that the increase in observed cell proliferation was due to the plant recombinant IL-10 and not other factors present in the purified plant fraction. Similar results were observed for insect-produced IL-10 (hIL-10).

Collectively, these results demonstrate that plant-produced IL-10 is processed and assemble into a biologically active dimeric form of IL-10.

Following the detection of IL-10 transcripts and protein in the transgenic plants crude protein extracts containing prIL-10 the demonstration of bioactivity of human IL-10 is determined in vitro by its effect on T cell proliferation in response to lectins (PHA) as well as in standard mixed lymphocyte responses (MLR). Plant extract or purified IL-10 from plant extract is added to media containing human lymphocytes, at a concentration ranging from 1-100 ngm/ml. Proliferation is determined in PHA cultures and mixed lymphocyte reaction cultures at days 3-6 by standard $^3$H-thymidine incorporation proliferation assays.

Surface expression of MHC class II proteins is determined on human lymphocytes activated by either PHA or ConA in the presence of increasing concentrations of IL-10. And compared to control plant extracts.

Peripheral blood lymphocytes are stimulated with LPS (1-10 µ/ml) for 24-48 hours, and levels of cytokines determined by ELISA or bioassay. Inhibition is determined as well, at the RNA level, by Northern blot analysis.

IL-10 is beneficial in prevention of lethal endotoxemia. Following appropriate approval the effect of IL-10 purified from plant extract on endotoxic injury in BALB/c mice is tested. $E.$ $coli$ is administered interperitoneally or intravenously in the presence of various amounts of recombinant munne IL 10. Plant extract is given to mice orally in addition to purified IL-10 from plants given intravenously. Outcomes are determined by survival of mice, which is essentially zero percent in untreated mice. Appropriate controls include PBS treated mice as well as mice given standard animal chow.

IL-10 deficient mice develop bowel inflammation and lesions resembling inflammatory bowel disease, which is improved by systemic IL-10. To test whether oral plant IL-10 can prevent bowel disease in an IL-10 deficient mouse model of IBD, transgenic plant material is administered to IL-10 null mice daily from age 4 weeks and mice are assessed for the presence of bowel lesions from age 8 to 30 weeks by weight gain and histology of tissue.

Creation of Leaf Material for Inclusion in Mouse Chow

Seed from single high expressing homozygous line, G7-9-2 (low nicotine tobacco) created using standard techniques (Miki et al. 1999. Biotechnol Agric For 45:336-354) as described earlier, was germinated and seedlings transferred to pots filled with soil. The seedlings were grown in controlled environment chambers (Conviron) set at 21 EC with 16 h day-length until approximately 10 weeks old. Leaves were removed from plants, quick frozen in liquid N2, and lyophilized.

Concentration of IL10 in Tissue (µg/g Dry Weight)

The concentration of recombinant IL10 in the leaf tissue was determined as follows: lyophilized leaf tissue (1 g of dry weight) was ground in 2 ml of extraction buffer (phosphate buffered saline (PBS) pH 7.4, 0.05% (v/v) Tween 20, 2% (w/v) polyvinylpolypyrrolidone (PVPP), 1 mM phenylmethylsulfonylfluoride (PMSF), 1 ug/ml Leupeptin) and clarified by centrifugation at 13,000 g for 15 min at 4° C. The supernatant containing total soluble proteins was analyzed directly in a commercial human IL-10 ELISA using standard protein and antibodies as per the supplier's protocol (Pharmingen). Protein was quantitated using the Bradford method (Bradford. 1976 Anal. Biochem. 72:248-254). The lyophilized tissue was found to contain 2.234 mg plant recombinant IL10 per gram of dry tissue.

Ingredients of Diet

Mouse chow with either 10% (w/w) or 20% (w/w) of lyophilized plant tissue (G7-9-2) with a concentration of 2.234 mg/g dry weight of plant recombinant IL10 was prepared. In addition similar chow was prepared with either 10% (w/w) or 20% (w/w) of untransformed (81V9) lyophilized tobacco tissue. Control chow with no plant tissue was also prepared. One hundred grams of 10% plant tissue chow contained 20 g lyophilized tobacco tissue, 44 g of dextrose, 12 g of corn starch, 17 g of casein, 5 g cellulose, 4 g minerals, 2 g salt supplement, 1 g of vitamins, 4.5 g of fat and and 0.5 g of corn oil. One hundred grams of 20% plant tissue chow contained 20 g lyophilized tobacco tissue, 40 g of dextrose, 11 g of corn starch, 17 g of casein, 4 g minerals, 2 g salt supplement, 1 g of vitamins, 4.5 g of fat and 0.5 g of corn oil. One hundred grams of control chow contained 50 g of dextrose, 15 g of corn starch, 18 g of casein, 5 g cellulose, 4 g minerals, 2 g salt supplement, 1 g of vitamins, 4.5 g of fat and 0.5 g of corn oil. The amount of chow eaten by each group and the amount of water consumed was recorded.

Mouse Feeding Trials

An experiment was conducted for 30 days with 5 groups of 6 week old IL10 null mice (Kuhn et al. 1993. Cell 75:263-270), with four males and four females in each group. Body weight of the mice ranged between 17 and 21 grams. All mice were fed 5 g of chow per day and were housed in micro-isolator cages. The first group of mice received control chow, the second group chow with 10% 81V9, the third group chow with 20% 81V9, the fourth group chow with 10% G7-9-2, the fifth chow with 20% G7-9-2. The drinking water of all mice contained 1.16 ml/l of an H2 antihistamine (ranitidine) to reduce gastric acidity and limit acid induced loss of biological activity of the IL10 in the plant tissue (Grimley et al 1997. Aliment Pharmacol. Ther. 11:875-879; Syto et al. 1998. Biochem. 37:16943-16951). All mice were sacrificed at the end of 30 days.

Pathology

Figure 17:
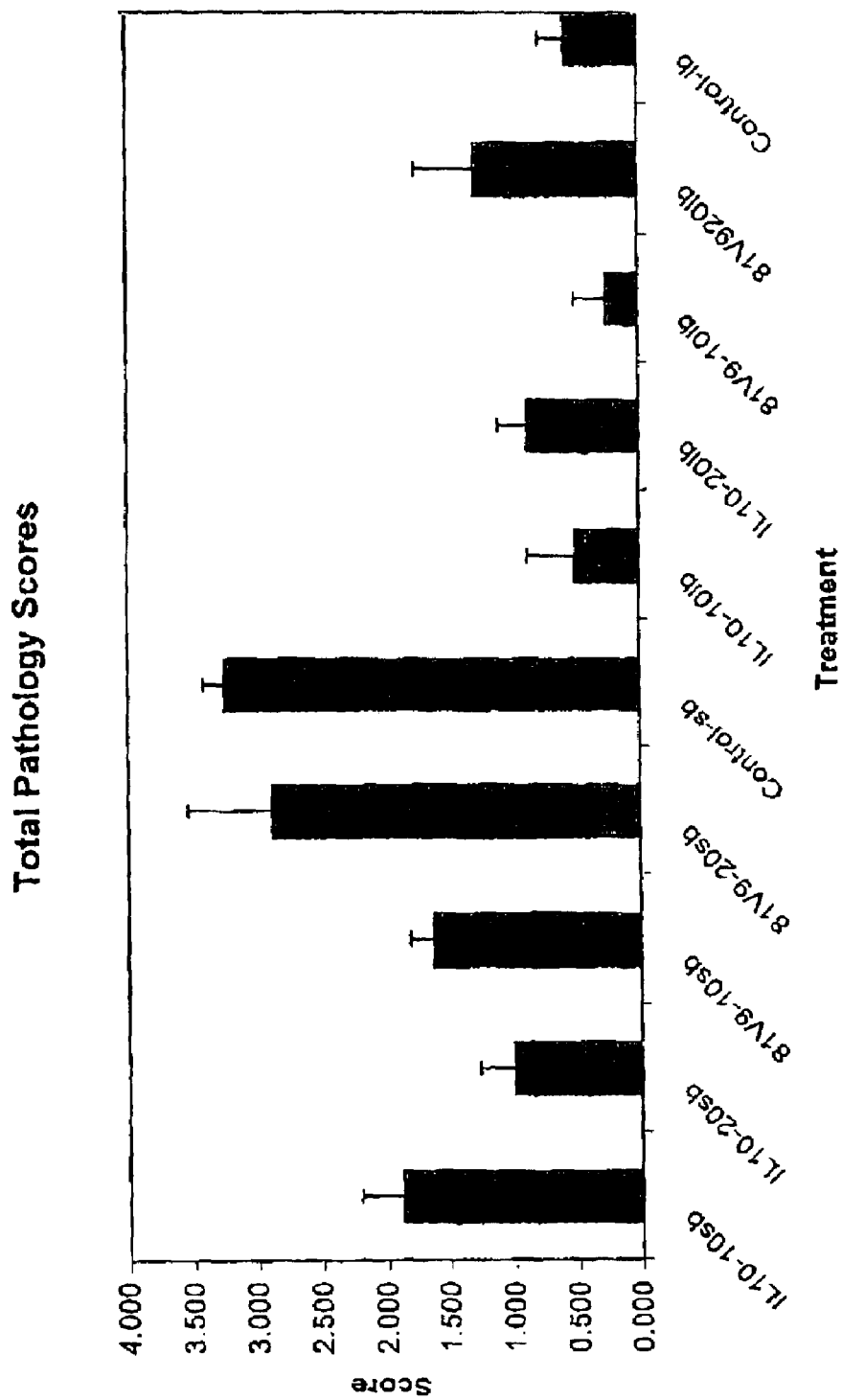
FIG. 17 graphically depicts total pathology scores for the large bowel (1b) and small bowel (sb) of 5 groups of IL10 null mice fed control chow (Control), chow plus 10% 81V9

Colon sections were taken and sections prepared. Colon sections were randomized and interpreted blindly. Grading system for mice given IL-10 or IL-4 includes the presence of ulceration, epithelial injury, infiltration and the presence of lymphoid follicles. Each variable was scored from 0 (which is normal pathology without infiltrate or injury), to 4 (which represents severe ulceration, extensive epithelial injury with loss of crypts, infiltration of the lamina submucosa as well as the lamina muscularis and >3 lymphoid follicles). Scores from individual mice were decoded and analysed using analysis of variance. The results are presented in FIG. 17. The results suggest that mice fed G7-9-2 tobacco (comprising IL-10) at a concentration of 20% (w/w) had significantly lower histological scores than mice fed 81V9 tobacco (P=0.003) or control chow (P<0.001).

The predominant pathology in IL-10 deficient mice appears to be within the small bowel, with large bowel involvement increasing in mice housed in facilities in which there is a higher rate of pathogen infections within various colonies. Consistent with this, given the clean facilities that the mice were treated in, the predominant pathology was found in the small bowels of mice, and greatest in those mice given control chow or vector control chow. The greatest benefit was found in the small bowel of mice given 20% of their total daily protein in the form of interleukin-10 expressing low nicotine tobacco plant material. In these treated mice, the level of pathology was essentially equivalent to normal mice without inflammatory bowel disease.

Example 4

Alkaloid Levels in Leaf Tissue of Low-Nicotine, Low-Alkaloid Tobacco Plants

In order to establish concentrations of tobacco alkaloids in normal and low-nicotine, low-alkaloid tobacco plants a field trial was conducted during the summer of 1997 Transplants of Delgold, a tobacco cultivar with normal alkaloid concentrations and 81V-9 the non-food bioreactor genotype used for this present invention were started in mid April in a cold frame greenhouse located at the Delhi Research Station in Ontario Canada. The two cultivars were transplanted into a 1.2×2 m plots at a density of approximately 133,000 plants per hectare. The trial employed a randomized complete design with four replications and was fertilized with 60 kg nitrogen per hectare. The trial was harvested 40 days after planting, the tissue was roughly chopped, quick frozen in liquid nitrogen and held at −70° C. until ready for analysis. The tissue was then lyophilized and tobacco alkaloid concentrations in the tissue determined by gas chromatography. For this analysis approximately 1 gram of lyophilized tobacco tissue was ground to pass a 20 mesh screen and was then extracted with dichloromethane and aqueous sodium hydroxide by shaking for 10 min on a wrist action shaker. The dichloromethane layer was filtered and collected for alkaloid analysis. The internal standard method was used with anethole being that standard. All gas chromatographic analyses were performed on an Hewlett Packard 5890 series II using a DB5 60 m×0.25 mm i.d. column with splitless injection and a 2 μl sample volume. Total tobacco alkaloid concentrations were found to be 35 fold lower in the low-nicotine, low-alkaloid tobacco plants compared to the normal tobacco cultivar. A similar pattern is found for the level of nicotine (see Table 1).

TABLE 1

Concentration (mg/g) of the various tobacco alkaloids found in ihe leaves of normal tobacco and in the non-food bioreactor.

| Cultivar | Nicotine | Myosmine | Anabasine mg/g | Anatabine | Total | % of total nicotine | % of total alkaloid |
|---|---|---|---|---|---|---|---|
| Delgold | 7.892a* | 0.000a | 0.013a | 0.000a | 7.923a | 100 | 100 |
| 81V-9 | 0.209b | 0.000a | 0.018a | 0.020b | 0.227b | 2.6 | 0.28 |

*means followed by a different letter are significantly from different from each other at P-0.05

Example 5

Glutamic Acid Decarboxylase (GAD) Expression

Cloning of Genes Encoding Human Glutamic Acid Decarboxylase, GAD65 and GAD67 from Human Brain Tissue was performed as follows:

Preparation of RNA

Tissue of frozen human brain sufficient to produce cDNA using PCR, was obtained from autopsy material. Total RNA was prepared from these samples using RNA TRIZOL kit (Life Technologies, Inc.) according to the manufacturer's instructions. Poly(A)+ mRNA was selected by oligo(dT)-cellulose chromatography (Pharmacia). The concentration and purity of isolated Poly(A)+ mRNA were determined at $A_{260}$ and $A_{280}$.

RT-PCR of RNA.

Human mRNA (250 ng used as template) for GAD65 was reverse-transcribed using a random primer (oligo (dT)$_{12-18}$) and SuperScript II reverse transcriptase (Life Technologies, Inc.) according to the manufacturer's instructions in a total reaction volume of 20 μl. For isolation of human GAD65, single-stranded cDNA (1 μl) was amplified with GAD65 gene-specific oligonucleotide primers;

```
Forward primer:                          (SEQ ID NO:15) and
5'-AATTCCATGGCATCTCCGGGCTCTGGC-3'
       NcoI Reverse Primer:                          (SEQ ID NO:16).
5'-ATAATCTAGATTATAAATCTTGTCCAAGGCGTTC-3'
      XbaI
```

(NcoI and XbaI were the two new restriction enzyme cleavage sites created to facilitate subsequent cloning)

in a total reaction volume of 100 μl containing NH$_4$ buffer, 1.5 mM MgCl$_2$, 200 μM of dNTP, 0.2 μM of each primer and 2.5 units of high fidelity DNA polymerase Pwo (Boehringer Mannheim). The PCR reaction was performed as follows: 3 min at 94° C., followed by 30 cycles at 94° C. for 1 min, 55° C. for 1 min and 72° C. for 2 min, followed by a final extension at 72° C. for 10 min. The PCR products were purified by agarose-gel electrophoresis and extracted using a gel extraction kit (QIAGEN Inc.) The purified cDNA was digested with both NcoI and XbaI, and ligated to modified plasmid vector pBluescript at the same sites.

For the isolation of human GAD67, single-stranded cDNA (1 μl) was amplified with GAD67 gene-specific oligonucleotide primers:

```
Forward primer:                          (SEQ ID NO:17)
5'-TTAATCTAGACCATGGCGTCTTCGACCCCATCTTCG-3'
     XbaI   NcoI Reverse primer:                          (SEQ ID NO:18)
5'-TTAATCTAGATTACAGATCCTGGCCCAGTCTTTC-3'
     XbaI
```

(XbaI and NcoI were the new restriction enzyme cleavage sites created to facilitate subsequent cloning).

In a total reaction volume of 100 μl containing NH$_4$ buffer, 1.5 mM MgCl$_2$, 200 μM of dNTP, 0.2 μM of each primer and 2.5 units of high fidelity DNA polymerase Pwo (Boehringer Mannheim). The PCR reaction was as follows: 3 min at 94° C., followed by 30 cycles at 94° C. for 1 min, 55° C. for 1 min and 72° C. for 2 min, followed by a final extension at 72° C. for 10 min. The PCR products were purified by agarose-gel electrophoresis and extracted by using gel extraction kit (QIAGEN Inc.) The purified cDNA was digested with XbaI, and ligated to modified plasmid vector PBluescript at the same site.

DNA Sequencing

The sequence of both human GAD65 and human GAD67 cDNA was determined in both directions by the dideoxynucleotide chain-termination method using DNA oligonucleotide primers complementary to different sequences of the coding region. The sequence was compared with published sequence of human brain and islet GAD65 and GAD67. A comparison of the sequence of our isolated human brain GAD65 and GAD67 gene with published sequence of human brain GAD65 and GAD67 demonstrated that they are identical.

Construction of Plant Expression Vectors for Human GAD65.

To construct a plant expression vector for human GAD65, human GAD65 cDNA, was amplified with PCR using the primers 5'-AATCCATGGCATCTCCGGGCTCTG-3' (SEQ ID NO:19) and

5'-ATA TCTAGATAAATCTTGTCCAAGGCG-3' (SEQ ID NO:20)

and the purified PCR product was then ligated to plasmid pTRL-GUS in replacement of GUS gene. The resulting GAD65 expression cassette was then cloned into vector pBinI9 and then transferred into *A. tumefaciens* LBA4404. Transformation of *Nicotiana tabacum* cv. SR1 was by leaf disc cocultivation with *A. tumefaciens* LBA4404 harbouring hGAD65 using the procedures described previously (Ma et al, 1997). Mature plants were generated from regenerated shoots under antibiotic selection in hormone-free rooting medium, and then subjected to screening for recombinant protein expression. Transgenic plants expressing the highest levels of transgene proteins were selected for long-term maintenance.

Western Blot Analysis and Chemiluminescent ELISA

Tobacco plants (*Nicotiana tabacum* cv. SR1) were transformed with the plant expression vectors comprising a human GAD65 gene by *A. tumefaciens*-mediated leaf explant transformation method. The regenerated tobacco plants were then analyzed for the presence of hGAD65 DNA, its specific mRNA transcripts and protein products. Integration of human GAD65 cDNA into the plant genome was confirmed by polymerase chain reaction (PCR) using GAD65 specific primers of genomic DNA, and mRNA transcripts were demonstrated by northern blot analysis using P32-labeled DNA probes representing the structural gene of hGAD65. Immunoblot analysis of plant recombinant GAD65 was performed according to the following procedure. The leaf tissue from GAD65 transgenic tobacco was homogenized on ice in extraction-buffer (25 mM Tris-HCl, pH 8.0, 50 mM NaCl, 0.1% SDS, 2 mM 2-mercaptoethanol, 1 mM PMSF, 2 mg/ml Leupeptin, 2 mg/ml Aprotitin, and 2 mg/ml Pepstatin A). The tissue homogenates were centrifuged at 4° C. for 15 min at 14,000 g and the concentration of proteins in the supernatants was determined by protein assay (Bio-Rad, Canada). Samples of proteins were separated by SDS polyacrylamide gel electrophoresis, proteins were transferred onto PDF membrane by electroblotting and the recombinant protein was detected by incubation with anti-human GAD65 antibody (Cedarlane, Hornsby) and a horseradish peroxidase-conjugated secondary antibody and ECL detection reagents (Amersham). Immunoblot analysis of protein homogenates from transgenic tobacco leaf tissues showed a single protein band of the correct size (kDa 65, FIG. 1, lanes 1 and 2), while no protein band was recognized with the same GAD antibody in extracts from control tobacco plants transformed with empty vector (lane C) (FIG. 1). An *E. coli*-derived recombinant GAD67 standard was included for the purpose of densitometry comparison. The level of plant-derived recombinant GAD65 expression was determined by scanning the signal strength of the applied GAD leaf extracts and purified *E. coli*-derived recombinant GAD67 of known concentration on the obtained blots using a pdi white light scanner (Raytest). The expression level of GAD65, estimated from blot densitometry, was found to be approximately 0.04% of total soluble proteins.

Example 6

Transgenic Plant Feeding Trials

NOD mice were housed according to guidelines of the Canadian Council on Animal Care and were screened for bacterial and viral pathogens. Parental colony incidence of diabetes in female mice is 70-80% by 30 weeks. Female pre-diabetic NOD mice were started at 4 weeks of age. Fresh mIL-4 and hGAD65 transgenic tobacco leaf tissues were homogenized in liquid nitrogen and the tissue homogenates were added to feed up to 12% (w/w) of diet. The amount of mouse IL-4 was calculated to deliver approximately 10-12 μg per mouse daily if completely digested, whereas the amount of human GAD65 fed per mouse daily was approximately 8-10 μg. Mice were caged as a group of 4. Control mice received an equivalent amount of corresponding leaf tissue from vector-transformed tobacco. Mice were monitored for glucose levels in urine weekly by using TES-TAPE Lilly, Indianapolis, Ind.), with serum testing to confirm diabetes (>16.7 mmol/l on two consecutive days (Glucoscan 2000 Strips, Lifescan, Milpitas, Calif.).

The onset of insulitis is monitored by immunohistochemical analysis of pancreatic tissue. The pancreata of NOD mice were harvested at 10 weeks of age. Pancreatic tissue was removed, fixed with 10% buffered formalin, embedded in paraffin and sectioned at 5 μm intervals. The incidence and severity of insulitis was examined by hematoxylin and eosin staining. A minimum of 15 islets from each mouse was examined, and the degree insulitis was evaluated based on the following semi-quantitative rating system: score 0, normal (no mononuclear cells infiltrating islets); score 1, peri-insulitis only (mononuclear cells surrounding islets, but no infiltration of the islet); score 2, moderate insulitis (mononuclear cells infiltrating <50% of the islet); and score 3, severe insulitis (>50% of the islet tissue infiltrated by lymphocytes). The results indicate that there was reduction, but not absence of insulitis in treated mice.

Suppression of Diabetes

To determine whether combined administration of GAD and IL-4 plant prevented diabetes, mice were supplemented with hGAD65 plus mIL-4 plant leaf tissues in their diet from 5 weeks to 30 weeks of age. The amount of hGAD65 delivered daily per mouse was estimated to be approximately 8 to 10 μg, whereas the amount of IL-4 delivered daily per mouse was approximately 10 to 12 μg. Control groups of mice were fed tobacco leaves transformed with empty vector or hGAD65 or mIL-4 transgenic leaf tissues alone. The mice were followed for the development of hyperglycemia. NOD mice receiving GAD65 plus IL-4 transgenic plant tissues showed a significant decrease in the incidence of developing diabetes (<30%, 2 out of 7 NOD mice at 30 weeks of age), compared with the GAD65 plant alone fed mice (80%, 8 out of 10 NOD developed diabetes) or IL-4 plan alone fed mice (100%, 10 out of 10 NOD mice developed diabetes) or empty vector transgenic plants fed mice (>60%, 5 out of 8 developed diabetes).

Serum IgE Ab Quantification

IL-4 mediates immunoglobulin class switch to IgE production (Ryan, 1997), which is associated with the induction of an allergic response. To determine whether oral administration of IL-4 plants elevates the level of IgE Ab production in NOD mice treated with both GAD and IL-4 plants or IL-4 plants alone, GAD plus IL-4 treated, IL-4 treated and control plant-treated mice were monitored for their relative serum IgE concentrations. The levels of IgE Abs in serum samples collected from female NOD mice were determined by ELISA. Briefly, serum samples were added at appropriate dilutions to microtiter plates coated with 2 µg/ml of purified anti-mouse IgE capture mAb (clone R35-72; PharMingen). Biotinylated anti-mouse IgE mAb (2 µg/ml, clone R35-118; PharMingen) together with avidin-peroxidase and ABTS substrate were used for detection. No serum IgE concentrations were found to be significantly elevated in GAD plus IL-4 treated or IL-4 treated mice compared to that in control-treated mice. Thus, administration of low dose IL-4 does not induce an appreciable increase in serum IgE concentration.

Treatment with GAD and IL-4 Transgenic Plants Prevents Adoptive Transfer of IDDM.

NOP-scid mice 8-10 weeks of age received a single i.p. injection of $10 \times 10^6$ spleen cells from diabetic donors mixed with $10 \times 10^6$ spleen cells from nondiabetic NOD mice fed transgenic GAD and IL-4 plants. Control mice received a single i.p. injection of $10 \times 10^6$ spleen cells from diabetic donors. Recipient mice were monitored for diabetes up to 8 weeks. Results showed that 50% of the mice receiving a mixture of splenic mononuclear cells from GAD+IL-4 treated and diabetic mice developed diabetes at the end of 8 weeks post transfer, while 100% of the mice receiving only diabetic splenic cells developed IDDM (FIG. 4). This suggests that treatment with both GAD and IL-4 plants induces regulatory T cells in prediabetic NOD mice that are capable of blocking tissue destruction by a diverse, activated effector T-cell population.

All scientific publications and patent documents are incorporated herein by reference.

The present invention has been described with regard to preferred embodiments. However, it will be obvious to persons skilled in the art that a number of variations and modifications can be made without departing from the scope of the invention as described herein. In the specification the word "comprising" is used as an open-ended term, substantially equivalent to the phrase "including but not limited to", and the word "comprises" has a corresponding meaning. Citation of references is not an admission that such references are prior art to the present invention.

REFERENCES

Abrams, J. S., M. G. Roncarolo, H. Yasel, U. Anderson, G. Gleich, J. Silver (1992) Strategies of anti-cytokine monoclonal antibody development. Immunol. Rev. 127, 5-24.

Bradford M. M. (1976) A rapid and sensitive method for the quantitation of microgram quantities of protein utilizing the principle of protein dye binding. Anal. Biochem. 72, 248-254.

Burnette W. H. (1981) Western blotting: electrophoretic transfer of proteins from SDS-polyacrylamide gels to unmodified nitrocellulose and radio-graphic detections with antibody and radioiodinated protein A. Anal. Biochem. 112, 195-203.

Chaplin J. F. (1977) Breeding for varying levels of nicotine in tobacco. In: Proc Amer Chem Soc, 173rd meeting, New Orleans.

Cornelissen B. J. C, R. A. M Hooft van Huijsduijnen, L. D. Van Loon & J. F. Bol (1986) Molecular characterization of messenger mRNAs for "pathogenesis-related" proteins 1a, 1b and 1c, induced by TMV infection of tobacco. EMBO J. 5, 37-40.

Denecke J., J. Botterman & R. Deblaere (1990) Protein secretion in plant cells can occur via a default pathway. Plant Cell 2, 51-59.

Fourney R. M., J. Miyakoshi, R. S. Day III & M. C. Paterson (1988) Northern blotting: efficient RNA staining and transfer. Focus 10:1, 5-7.

Fiocchi C. (1993) Cytokines and animal models: a combined path to inflammatory bowel disease pathogenesis. Gastroenterology 104:1202-1219.

Frisch, D. A., Harris-Haller, L. W., Yokubaitis, N. T., Thomas, T. L., Hardin, S. H., and Hall, T. C. (1995). Complete sequence of the binary vector Bin 19. Plant Mol. Biol. 27, 405-409.

Gengenheimer P (1990) Preparation of Extracts from Plants. Methods of Enzymology 182, 184-185.

Haq T. A., H. S. Mason, J. D. Clements, C. J. Artzen (1995) Oral immunization with a recombinant bacterial antigen produced in plants. Science 268, 714-716.

Hiatt A., R. Cafferkey & K. Bowdish (1989) Production of antibodies in transgenic plants. Nature 342, 76-78.

Horsch R. B., J. Fry, N. Hofmann, J. Neidermeyer, S. G. Rogers & R. T. Fraley. (1988) Leaf disc transformation. Plant Molecular Biology Manual A5, 1-9. Ed. S. B. Gelvin, R. A. Schilperoort, D. P. S. Verma. Kluwer Academic Publishers. Dordrecht/Boston/London.

Kay R., A. Chan, M. Daly & J. McPherson (1987) Duplication of CaMV 35S promoter sequences creates a strong enhancer for plant genes. Science 236, 1299-1302.

Kuhn R. Lohler J, Rennick D, Rajewsky K, Muller W (1993) Interleukin-10 deficient mice develop chronic enterocolitis. Cell 75:263-274.

Kunkel T. A. (1985) Rapid and efficient site-specific mutagenesis without phenotypic selection. Proc. Natl. Acad. Sci. USA 82, 488-492.

Lehrach H., D. Diamond, J. M. Wozney & H. Boedtker. (1977) RNA molecular weight determinations by gel electrophoresis underdenaturing conditions; a critical reexamination. Biochemistry 16, 4743.

Ma J. K. C., M. Hein (1995) Immunotherapeutic potential of antibodies produced in plants. TibTech 13, 522-527.

Mason H. S., J. M. Ball, J-J. Shi, X. Jiang, M. K. Estes, C. J. Amtzen (1996) Expression of Norwalk virus capsid protein in transgenic tobacco and potato and its oral immunogenicity in mice. Proc. Nat. Acad. Sci. 93, 5335-5340.

Miki, B. L. A., McHugh, S. G., Labbe, H., Ouellet, T., Tolman, J. H., and Brandle, J. E. (1998) Transgenic tobacco: gene expression and applications. Biotechnology in Agriculture and Forestry (in press)

Motanari L., P. Fantozzi, S. Pedone (1993) Tobacco fraction 1 (F1P utilization of oral feeding and enteral feeding of patients. 1 Heavy Metal evaluation. Food Saci. Tech. 26, 259-263.

Otsuka T., D. Vallaret, T. Yokota, Y. Takebe, F. Lee, N. Arai, K. Arai (1987) Structural analysis of the mouse chromosomal gene encoding interleukin-4 which expresses B cell, T cell and mast cell stimulating activities. Nucl. Acid. Res. 15, 333-334

Palmiter R. D. (1974) Magnesium precipitation of ribonucleoprotein complexes: Expedient techniques for the isolation of undegraded polysomes and messenger ribonucleic acid. Biochemistry 13, 3606-3615.

Perlak F J, Fuchs R L, Dean D A, McPherson S L, Fischoff D A (1991) Modification of the coding sequence enhances plant expression of insect control protein genes. Proc Natl Acad Sci 88:3324-3328.

Rapoport M. J., D. Zipris; A. H. Lazarus, A. Jaramillo, D. V. Serreze, E. H. Leiter, P. Cyopick, J. S. Danska, T. L. Delovitch (1993) IL-4 reverses thymic T cell proliferative unresponsiveness and prevents diabetes in NOD mice. J. Exp. Med. 178, 87-99.

Richards K., H Guilley, G. Jonard & G. Keith (1977) Leader sequence of 71 nucleotides devoid of G in tobacco mosaic virus RNA. Nature 267, 549-550.

Richards K., H. Guilley, G. Jonard & L. Hirth (1978) Nucleotide sequence at the 5' extremity of tobacco mosaic virus RNA. Eur. J. Biochem. 84, 513-519.

Schouten A et al. (1966) The C-terminal KDEL sequence increases the expression level of a single-chain antibody designed to be targeted to both the cytosol and the secretory pathway in transgenic tobacco. Plant Molec. Biol. 30, 781-793.

Sleat D. E., R. Jull, P. C. Turner & T. M. A. Wilson (1988) On the mechanism of translational enhancement by the 5'-leader sequence of tobacco mosaic virus RNA. Eur. J. Biochem. 175, 75-86.

Sijmons P. C., B. M. M. Dekker, B. Schrammeijer, T. C. Verwoerd, P. J. M. van den Elzen & A. Hoekema (1990) Production of correctly processed human serum albumin in transgenic plants. Bio/Technology 8, 217-221.

Vieira, P., de Waal-Maleyfyt, R., Dang, M. N., Johnson, K. E., Kastelein, R., Fiorentino, D. F., deVries, J. E., Roncarolo, M. G., Mosmann, T. R., and Moore, K. W. (1991) Isolation and expression of human cytokine synthesis inhibitory factor cDNA clones: homology to Epstein-Barr virus open reading frame BCRF1. Proc. Natl. Acad. Sci. U.S.A. 88, 1172-1176.

von Heijne G. (1986) A new method for predicting signal cleavage sites. Nucl. Acids Res. 14, 4683-4690.

Woodleif W. G., J. F. Chaplin, C. R. Campbell, D. W. DeJong (1981) Effect of variety and harvest treatments on protein yield of close grown tobacco Tobacco Sci. 25, 83-86.

The embodiments of the invention in which an exclusive property of privilege is claimed are defined as follows:

1. A method of reducing an inflammatory response in a mammal said method comprising orally administering an effective amount of a plant that is stably transformed with a nucleic acid sequence that encodes IL-4 or IL-10, or plant matter obtained from said plant, wherein said plant matter comprises IL-4 or IL-10, and is minimally processed prior to administration to said mammal.

2. A method of reducing an inflammatory response in a mammal said method comprising orally administering an effective amount of a plant that is stably transformed with a nucleic acid sequence that encodes IL-10, or plant matter obtained from said plant, wherein said plant matter comprises IL-4 or IL-10, and minimally processed prior to administration to said mammal, wherein the inflammatory response is inflammatory bowel disease.

3. The method of claim 2, wherein said inflammatory bowel disease comprises ulcerative colitis or Crohn's disease.

4. The method of claim 1, wherein in said method, said plant is a tobacco plant.

5. The method of claim 1, wherein in said method, said plant is a low-nicotine, low-alkaloid tobacco plant.

6. A method of reducing an inflammatory response in a mammal comprising,
   i) expressing a IL-4 or IL-10 in a plant, and
   ii) orally administering an effective amount of said plant or plant matter that has been minimally processed to said mammal, wherein said plant or said plant matter comprises IL-4 or IL-10.

7. A method of reducing inflammatory bowel disease in a mammal comprising,
   i) expressing IL-10 in a plant, and
   ii) orally administering an effective amount of said plant or plant matter that has been minimally processed to said mammal, wherein said plant or said plant matter comprises IL-4 or IL-10.

8. The method of claim 6, wherein said inflammatory bowel disease comprises ulcerative colitis or Crohn's disease.

9. The method of claim 6, wherein in said step of expressing (step i) the plant is a tobacco plant.

10. The method of claim 9, wherein in said plant is a low-nicotine, low-alkaloid tobacco plant.

11. The method of claim 6, wherein in said step of orally administering (step ii), an effective amount of an antihistamine is co-administered with said plant or said plant matter.

12. The method of claim 7, wherein in said step of orally administering (step ii), an effective amount of an antihistamine is co-administered with said plant or said plant matter.

13. The method of claim 1, wherein an antihistamine is co-administered with said plant or said plant matter to said animal.

14. The method of claim 2, wherein an effective amount of an antihistamine is co-administered with said plant or said plant matter to said animal.

15. The method of claim 11, wherein said antihistamine is ranitidine.

16. The method of claim 12, wherein said antihistamine is ranitidine.

17. The method of claim 13, wherein said antihistamine is ranitidine.

18. The method of claim 14, wherein said antihistamine is ranitidine.

* * * * *